US012596089B2

(12) United States Patent
Ponte et al.

(10) Patent No.: US 12,596,089 B2
(45) Date of Patent: Apr. 7, 2026

(54) DEVICES, SYSTEMS, AND METHODS FOR ANTIMICROBIAL SUSCEPTIBILITY TESTING

(71) Applicant: Avails Medical, Inc., Menlo Park, CA (US)

(72) Inventors: Elizabeth Botbol Ponte, Menlo Park, CA (US); Creighton T. Buie, Austin, TX (US); Nitin K. Rajan, Palo Alto, CA (US); Andrew H. Theiss, Mountain View, CA (US); Suzanne Putney, San Francisco, CA (US); Eszter Deak, San Jose, CA (US); Meike Herget, Woodside, CA (US); Oren S. Knopfmacher, San Francisco, CA (US)

(73) Assignee: Avails Medical, Inc., Menlo Park, CA (US)

( * ) Notice: Subject to any disclaimer, the term of this patent is extended or adjusted under 35 U.S.C. 154(b) by 234 days.

(21) Appl. No.: 18/458,067

(22) Filed: Aug. 29, 2023

(65) Prior Publication Data

US 2024/0068983 A1     Feb. 29, 2024

Related U.S. Application Data

(60) Provisional application No. 63/507,956, filed on Jun. 13, 2023, provisional application No. 63/373,777, filed on Aug. 29, 2022.

(51) Int. Cl.
*G01N 27/333* (2006.01)
*C12Q 1/18* (2006.01)

(52) U.S. Cl.
CPC ........... *G01N 27/3335* (2013.01); *C12Q 1/18* (2013.01)

(58) Field of Classification Search
None
See application file for complete search history.

(56) References Cited

U.S. PATENT DOCUMENTS

| 2007/0072257 A1 | 3/2007 | Negulescu et al. |
| 2010/0304423 A1 | 12/2010 | Asai et al. |
| 2011/0028815 A1 | 2/2011 | Simpson et al. |
| 2011/0053241 A1 | 3/2011 | Den Tooner et al. |
| 2020/0324289 A1 | 10/2020 | Chen et al. |

FOREIGN PATENT DOCUMENTS

WO     WO 2024/050381     3/2024

*Primary Examiner* — J. Christopher Ball
(74) *Attorney, Agent, or Firm* — Levine Bagade Han LLP

(57) ABSTRACT

Various apparatus, systems, and methods for determining a susceptibility of an infectious agent to an anti-infective are disclosed. In one aspect, a system comprises a well plate, a sensor array lid configured to cover the well plate, and a reader for receiving the well plate covered by the sensor array lid. The well plate comprises wells including test wells comprising an anti-infective and at least one control well devoid of the anti-infective. Each of the wells is configured to receive and contain a sample. The sensor array lid comprises a plurality of sensor units. Each of the sensor units is configured to extend into a well of the well plate. Each of the sensor units comprises an active electrode and a reference electrode used by the reader to detect any changes in the solution characteristics within the wells to determine the susceptibility of the infectious agent to the anti-infective.

20 Claims, 17 Drawing Sheets

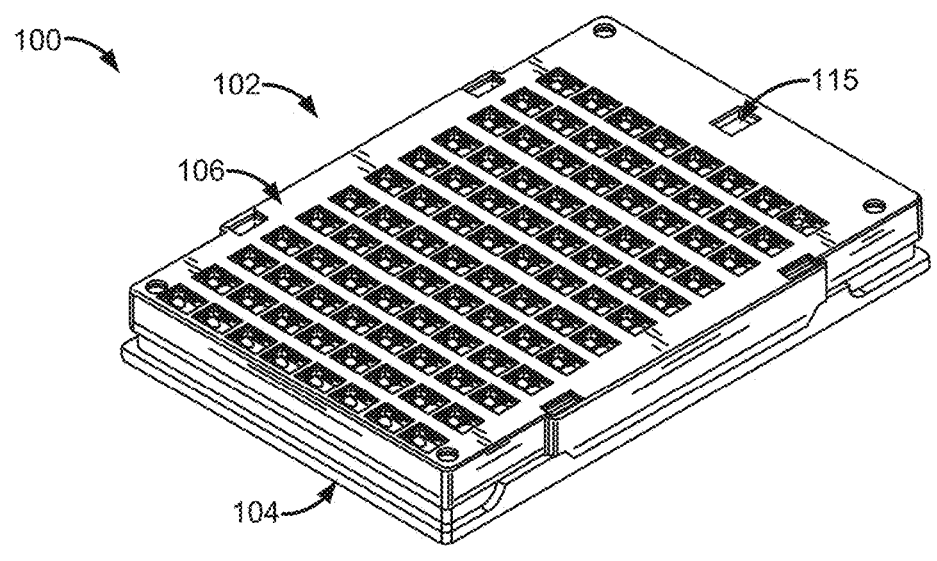
FIG. 1C
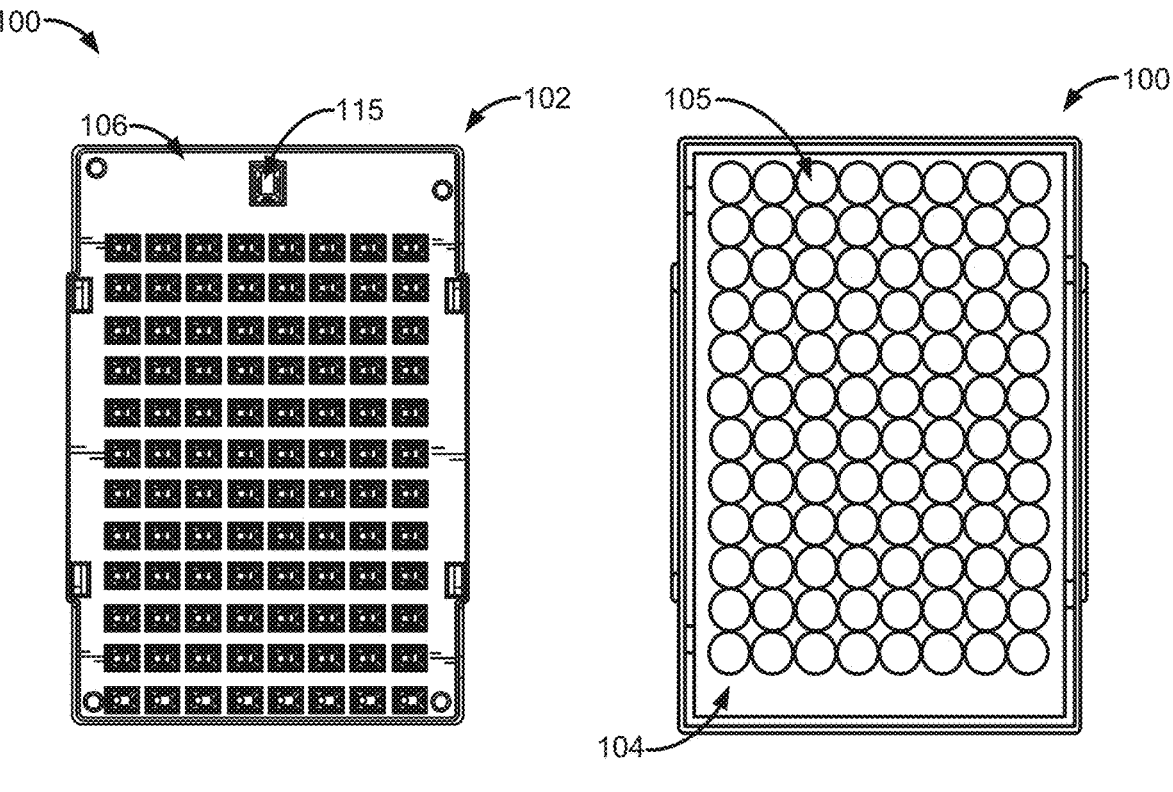
FIG. 1D          FIG. 1E

300

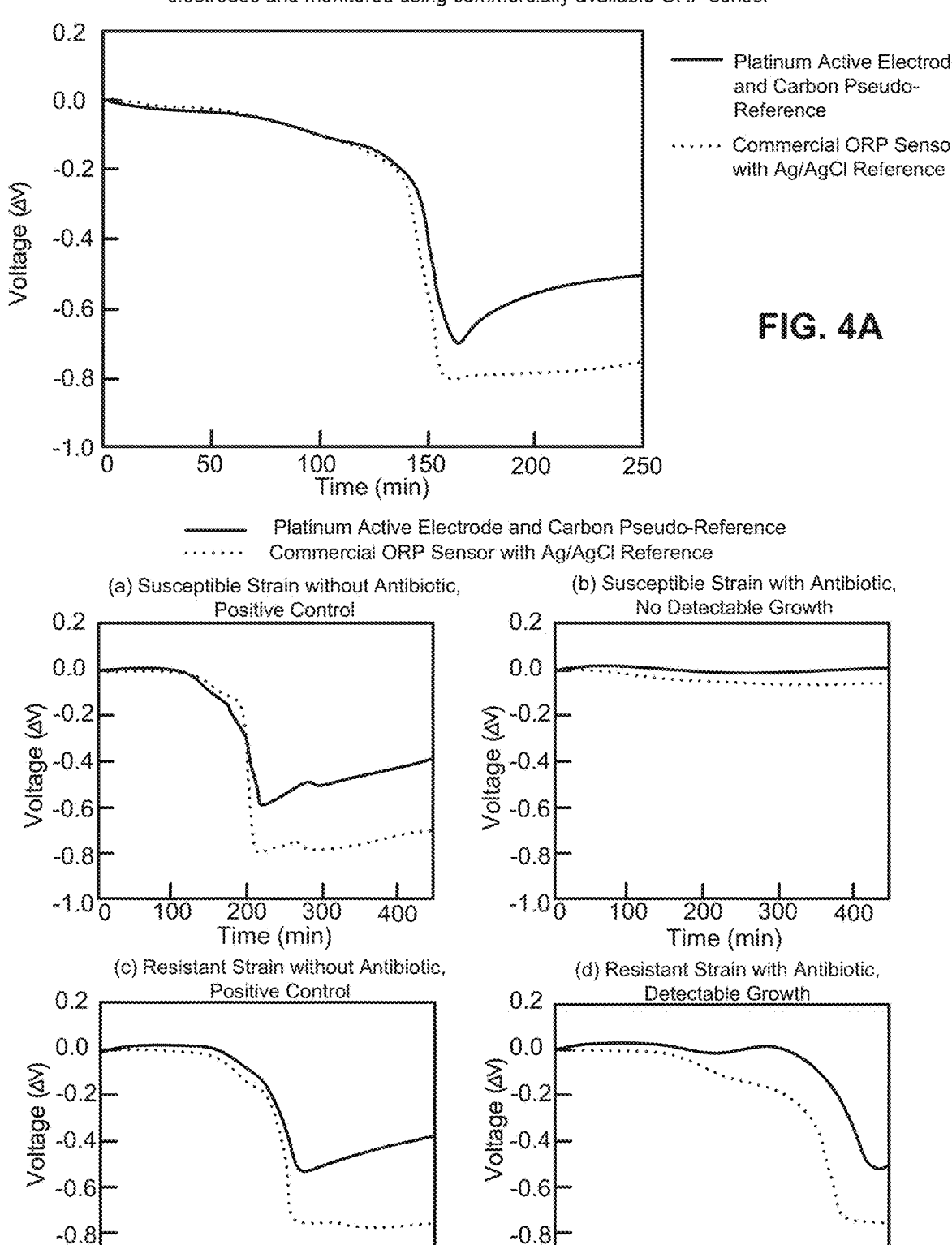

ORP growth curves of E. coli in Mueller Hinton Broth monitored using sensor units with screen-printed electrodes and monitored using commercially available ORP sensor ——— Platinum Active Electrode and Carbon Pseudo-Reference ······· Commercial ORP Sensor with Ag/AgCl Reference

FIG. 4A

——— Platinum Active Electrode and Carbon Pseudo-Reference
······· Commercial ORP Sensor with Ag/AgCl Reference (a) Susceptible Strain without Antibiotic, Positive Control (b) Susceptible Strain with Antibiotic, No Detectable Growth (c) Resistant Strain without Antibiotic, Positive Control (d) Resistant Strain with Antibiotic, Detectable Growth

FIG. 4B

ORP growth curves monitored using sensor units with
sputter deposited electrodes and monitored using
commercially available ORP sensor ORP growth curves of E. coli monitored using sensor units with electroplated electrodes

700

702

704

700

704

702

Performance Results for Gram-Negative Contrived PBCs

| Antibiotic | EA | CA | mD | MD | VMD | #MICs |
|---|---|---|---|---|---|---|
| AMK | 98.0% (287/293) | 95.2% (279/293) | 4.8% (14/293) | 0.0% (0/248) | 0.0% (0/31) | 293 |
| CRO | 99.5% (219/220) | 96.8% (213/220) | 2.7% (6/220) | 0.0% (0/99) | 0.9% (1/115) | 220 |
| ATM | 96.3% (260/270) | 93.3% (252/270) | 4.8% (13/270) | 3.1% (4/127) | 0.8% (1/129) | 270 |
| CFZ | 99.5% (207/208) | 95.7% (199/208) | 4.3% (9/208) | 0.0% (0/21) | 0.0% (0/172) | 208 |
| IPM | 98.5% (265/269) | 95.9% (258/269) | 3.7% (10/269) | 0.6% (1/179) | 0.0% (0/73) | 269 |
| TZP | 96.6% (283/293) | 92.5% (271/293) | 6.8% (20/293) | 1.2% (2/172) | 0.0% (0/92) | 293 |
| SXT | 98.8% (240/243) | 97.9% (238/243) | 0.0% (0/243) | 2.7% (4/146) | 1.0% (1/97) | 243 |
| TOTAL | 98.1% (1761/1796) | 95.2% (1710/1796) | 4.0% (72/1796) | 1.1% (11/992) | 0.4% (3/709) | 1796 |

FIG. 9A

Performance Results for Gram-Negative Prospective PBCs

| Antibiotic | EA | CA | mD | MD | VMD | #MICs |
|---|---|---|---|---|---|---|
| AMK | 100.0% (101/101) | 100.0% (101/101) | 0.0% (0/101) | 0.0% (0/101) | n/a (0/0) | 101 |
| CRO | 100.0% (87/87) | 98.9% (86/87) | 1.1% (1/87) | 0.0% (0/63) | 0.0% (0/21) | 87 |
| ATM | 93.1% (95/102) | 87.3% (89/102) | 5.9% (6/102) | 8.6% (7/81) | 0.0% (0/21) | 102 |
| CFZ | 100.0% (86/86) | 96.5% (83/86) | 3.5% (3/86) | 0.0% (0/38) | 0.0% (0/41) | 86 |
| IPM | 100.0% (96/96) | 100.0% (96/96) | 0.0% (0/96) | 0.0% (0/90) | 0.0% (0/6) | 96 |
| TZP | 85.9% (85/99) | 85.9% (85/99) | 10.1% (10/99) | 4.4% (4/91) | 0.0% (0/3) | 99 |
| SXT | 97.7% (85/87) | 97.7% (85/87) | 0.0% (0/87) | 3.3% (2/60) | 0.0% (0/27) | 87 |
| TOTAL | 96.5% (635/658) | 95.0% (625/658) | 3.0% (20/658) | 2.5% (13/524) | 0.0% (0/119) | 658 |

DEVICES, SYSTEMS, AND METHODS FOR ANTIMICROBIAL SUSCEPTIBILITY TESTING

CROSS-REFERENCE TO RELATED APPLICATIONS

This application claims the benefit of U.S. Provisional Application No. 63/507,956 filed on Jun. 13, 2023 and U.S. Provisional Application No. 63/373,777 filed on Aug. 29, 2022, the contents of which are incorporated herein by reference in their entireties.

TECHNICAL FIELD

The present disclosure relates generally to diagnostic devices, systems, and methods and, more specifically, to devices, systems, and methods for determining a susceptibility of an infectious agent to an anti-infective.

BACKGROUND

An increasing number of pathogenic bacteria are acquiring antibiotic resistance and new forms of resistance are continuously emerging with alarming speed across international boundaries. The US Center for Disease Control (CDC) calls antimicrobial resistance as one of the biggest public health challenges of our time. Every year in the US alone, over 2 million people acquire antibiotic-resistance infection and death rates are continuously rising. Providing a rapid low-cost antibiotic susceptibility test (AST) will be of increasingly vital importance in controlling this burgeoning problem. While current gold standard AST methods generally require burdensome and time-consuming overnight culturing, the time urgency of determining effective antibiotics has prompted a push for rapid AST that can provide results in a few hours. Speeding up AST results to provide targeted antibiotic therapy early on is key to improving patient survival. Delays in timely informative results lead physicians to administer broad-spectrum antibiotics, which can promote antibiotics resistance (AR).

Current lab procedures, such as blood collection to AST results and guided antibiotic therapy decisions, take multiple days and significant hands-on time of qualified personnel. The following steps are taken: i) blood culturing, ii) pathogen isolation from positive blood culture (PBC) on agar medium, iii) preparation of a standardized inoculum of 0.5 McFarland (MF) from the bacterial colonies, and iv) AST for identification of the antibiotic treatment. New technologies are under development, yet most still require a culture isolate as input.

Most rapid AST systems use light-based detection methods for determining AST results. This has significant drawbacks since the sample's blood content absorbs light and skews results.

Therefore, a solution is needed for a device that can detect phenotypic bacterial growth in the presence of blood and does not need to go through the bacterial isolation steps of other current detection methods. Such a solution should be cost-effective to manufacture. Such a solution should also not rely on labor-intensive techniques and provide accurate results. Such a solution should also allow for multiplex detection involving simultaneous readout of multiple wells to rapidly determine minimum inhibitory concentrations (MICs) from positive blood cultures (PBCs).

SUMMARY

Disclosed herein are diagnostic testing devices, systems, and methods for determining a susceptibility of an infectious agent to an anti-infective. In one embodiments, a system for determining a susceptibility of an infectious agent to an anti-infective is disclosed. The system can comprise a well plate comprising a plurality of wells. The plurality of wells can comprise test wells and at least one control well. Each of the wells can be configured to contain an aliquot of a sample comprising the infectious agent. At least one of the test wells can comprise the anti-infective and the control well can be devoid of the anti-infective.

In some embodiments, the sensor array lid can comprise a lid top and a flexible substrate coupled to an underside of the lid top. The sensor array lid can be configured to cover the well plate.

The flexible substrate can comprise a plurality of substrate strips or segments partially cut out from a remainder of the flexible substrate. At least one substrate strip or segment of the flexible substrate can curl or bend vertically downward relative to a surrounding portion of the flexible substrate.

An active electrode can be disposed on each of the substrate strips or segments curling or bending vertically downward and a reference electrode can be disposed on each of the substrate strips or segments curling or bending vertically downward. Each of the substrate strips or segments comprising the active electrode and the reference electrode can be considered a sensor unit.

The sensor array lid can comprise a plurality of sensor units extending from the underside of the sensor array lid. Each of the sensor units can be configured to extend into a well of the well plate such that the sensor unit is at least partially immersed in the aliquot of the sample within the well.

The system can further comprise a reader configured to receive the well plate and the sensor array lid covering the well plate within a receiving slot of the reader. The reader can comprise conductive contacts for contacting the active electrodes and the reference electrodes of the sensor units.

The reader can be configured to determine the susceptibility of the infectious agent to the anti-infective based on any changes in a solution characteristic of the aliquot of the sample within the test well comprising the anti-infective and any changes in the solution characteristic of the aliquot of the sample within the control well over a period of time.

Also disclosed is a method of determining a susceptibility of an infectious agent to an anti-infective. The method can comprise introducing aliquots of a sample comprising the infectious agent into wells of a well plate. The wells can comprise test wells and at least one control well. At least one of the test wells can comprise the anti-infective and the control well can be devoid of the anti-infective.

The method can also comprise covering the well plate with a sensor array lid. The sensor array lid can comprise a plurality of sensor units extending from an underside of the sensor array lid. Each of the sensor units can be configured to extend into one of the wells of the well plate such that the sensor unit is at least partially immersed in the aliquot of the sample within the well. Each of the sensor units can comprise an active electrode and a reference electrode.

The method can also comprise inserting the well plate covered by the sensor array lid into a reader. The reader can comprise conductive contacts for contacting the active electrodes and the reference electrodes of the sensor units. The method can also comprise determining the susceptibility of the infectious agent to the anti-infective based on any changes in a solution characteristic of the aliquot of the sample within the test well comprising the anti-infective and any changes in the solution characteristic of the aliquot of the sample within the control well over a period of time.

The method can further comprise diluting the sample with a dilutive solution to a dilution ratio of between about 1:1 to about 1:10000 prior to introducing the sample into the wells of the well plate. The method can also comprise incubating the well plate covered by the sensor array lid within the reader at an incubation temperature between about 30° C. and about 40° C.

In some embodiments, the well plate can comprise between 24 wells and 96 wells. The sensor array lid can comprise between 24 sensor units and 96 sensor units.

In some embodiments, the anti-infective within the test well can be lyophilized or dried.

In some embodiments, the anti-infective within the test well can be in aqueous form.

In some embodiments, any changes in the solution characteristics of the wells can be detected in the absence of any added reporter molecules added to the wells.

In some embodiments, the sample can comprise a bodily fluid or a bacterial culture derived therefrom. For example, the sample can be a positive blood culture.

In some embodiments, the infectious agent can comprise bacteria.

In some embodiments, the anti-infective can comprise a bacteriostatic anti-infective, a bactericidal anti-infective, or a combination thereof.

In some embodiments, the infectious agent can comprise fungi.

In some embodiments, the anti-infective can comprise an anti-fungal.

In some embodiments, the active electrode can comprise a redox-active material.

In some embodiments, the redox-active material can be a noble metal. For example, the noble metal can be platinum or gold. In other embodiments, the redox-active material can be a conductive metal oxide such as iridium oxide, ruthenium oxide, or any combinations or alloys of such materials with noble metals. In additional embodiments, the redox-active material can be a carbon-based electrode.

In some embodiments, the reference electrode can comprise a reference electrode material.

In some embodiments, the reference electrode material can comprise at least one of silver/silver chloride (Ag/AgCl) and carbon.

In some embodiments, the reference electrode material can be coated or covered by an ion exchange membrane.

In some embodiments, the ion exchange membrane can be a sulfonated tetrafluoroethylene based fluoropolymer-copolymer or a polyaromatic polymer anion exchange membrane.

In some embodiments, the lid top can comprise posts extending from the underside of the lid top. The posts can be configured to push or press against the substrate strips or segments such that the substrate strips or segments maintain their curled or bent configuration.

In some embodiments, at least one of the substrate strips or segments can be pushed or pressed by at least one of the posts such that a portion of the substrate strip or segment is substantially perpendicular to portions of the flexible substrate that are coupled to the lid top.

In some embodiments, the flexible substrate can be made in part of a flexible polymeric material.

In some embodiments, the flexible polymeric material can be made in part of polyethylene terephthalate (PET).

In some embodiments, the flexible polymeric material can be a flexible printed circuit board (PCB) material.

In some embodiments, the flexible PCB material can be polyimide.

In some embodiments, the flexible substrate can be made in part of a conductive metal substrate. For example, the conductive metal substrate can be stainless steel foil.

In some embodiments, the lid top can be made in part of at least one of polystyrene, polypropylene, and a cyclic olefin copolymer.

In some embodiments, at least one of the active electrode and the reference electrode can be a screen printed electrode (SPE) such that at least one of a redox-active material of the active electrode and a reference electrode material of the reference electrode is screen printed onto the flexible substrate.

In some embodiments, at least one of the active electrode and the reference electrode can be an electroplated electrode such that at least one of a redox-active material of the active electrode and a reference electrode material of the reference electrode is electroplated onto the flexible substrate.

In some embodiments, at least one of the active electrode and the reference electrode can be a sputter deposited electrode such that at least one of a redox-active material of the active electrode and a reference electrode material of the reference electrode is sputter deposited onto the flexible substrate.

In some embodiments, the sensor array lid can be disposable or one-time use.

In some embodiments, the flexible substrate can comprise an electrical contact pad disposed on the flexible substrate. The electrical contact pad can be left exposed by the lid top. The active electrode can be electrically connected to the electrical contact pad via conductive traces. The reference electrode can be electrically connected to the electrical contact pad via additional conductive traces.

In some embodiments, the reference electrode can be a pseudo reference electrode.

In some embodiments, the flexible substrate can be coupled to the underside of the lid top by at least one of a biocompatible adhesive and a fastener.

BRIEF DESCRIPTION OF THE DRAWINGS

FIG. 1C illustrates a perspective view of one embodiment of the testing device in an assembled configuration.

FIG. 1D illustrates a top plan view of the testing device in the assembled configuration.

FIG. 1E illustrates a bottom plan view of the testing device in the assembled configuration.

FIG. 4A illustrates an ORP bacterial growth curve obtained using an embodiment of the diagnostic device with screen-printed electrodes. Also shown is an ORP bacterial growth curve obtained using a commercially available ORP sensor.

FIG. 4B illustrate various ORP bacterial growth curves showing the growth behavior of susceptible and resistant bacteria in both test wells and control wells.

FIG. 9A is a table illustrating performance results for gram-negative contrived positive blood cultures (PBCs) in the presence of several antibiotics.

FIG. 9B is a table illustrating performance results for prospective gram-negative PBCs in the presence of several antibiotics

DETAILED DESCRIPTION

Variations of the devices, systems, and methods described herein are best understood from the detailed description when read in conjunction with the accompanying drawings. It is emphasized that, according to common practice, the various features of the drawings may not be to scale. The dimensions of certain features have been expanded or reduced for clarity and not all features may be visible or labeled in every drawing. The drawings are taken for illustrative purposes only and are not intended to define or limit the scope of the claims to that which is shown.

Figure 1A:
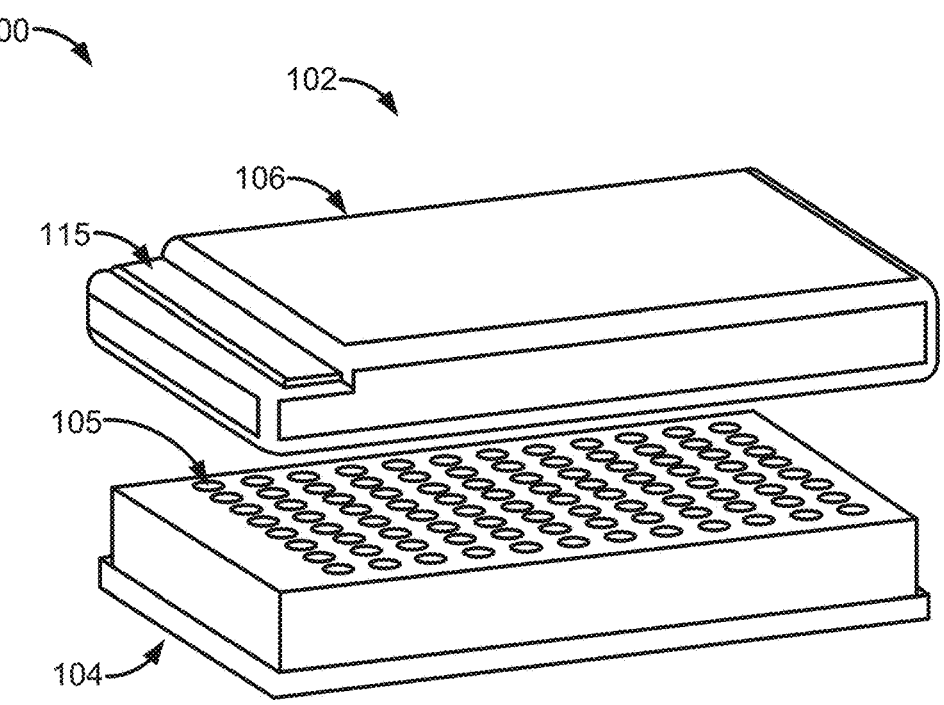
FIG. 1A illustrates a perspective view of one embodiment of a testing device comprising a sensor array lid and a well plate.

FIG. 1A illustrates a perspective view of one embodiment of a testing device 100 comprising a sensor array lid 102 and a well plate 104. The device 100 can be used as part of a system to determine the susceptibility of an infectious agent to an anti-infective. As will be discussed in more detail in the following sections, the system can further comprise a reader 700 (see FIGS. 7A and 7B) configured to receive and detect any changes in the solution characteristic of samples within the device 100. The system can assay the samples for microbial growth or lack thereof as part of an antibiotic susceptibility testing (AST) procedure.

As shown in FIG. 1A, the sensor array lid 102 can be configured to cover or cap the well plate 104 when placed on top of the well plate 104. The well plate 104 can comprise a plurality of wells 105 or microwells. For example, the well plate 104 can comprise between 12 wells and 192 wells. As a more specific example, the well plate 104 can comprise between 64 wells and 96 wells.

When the well plate 104 comprises 96 wells, the wells 105 can be arranged as an 8×12 array of wells. In other embodiments, the well plate 104 can comprise 48 wells, the wells 105 can be arranged as a 6×8 array of wells.

Each of the wells 105 can be designed to receive a sample comprising an infectious agent. The sample can be diluted prior to introducing aliquots of the sample to the wells 105.

In some embodiments, the wells 105 of the well plate 104 can comprise test wells and control wells. The test wells can each test comprise a type of anti-infective and the control wells can be devoid of any anti-infective (e.g., positive control wells).

For example, when a well plate 104 comprises 96 wells, between 1 and 20 wells of the well plate 104 can be used as control wells. In other examples, the number of control wells can be more than 20 wells (e.g., half of the wells can be control wells).

The wells 105 of the well plate 104 comprising the anti-infective can have the anti-infectives already present within the wells 105 or pre-loaded within the wells 105. In some embodiments, the anti-infective within the test wells can be lyophilized or dried. For example, the anti-infectives within the test wells can be in the form of a lyophilized disk, pellet(s), or powder.

In other embodiments, the anti-infectives within the test wells can be in aqueous form.

In some embodiments, the anti-infectives can be added, disposed, or otherwise introduced into the wells 105 of the well plate 104 prior to introducing aliquots of the sample into the wells 105 (the test wells and the control wells).

In some embodiments, each well plate 104 can comprise a plurality of anti-infectives such that some of the wells 105 of the well plate 104 are dedicated to a specific anti-infective and other wells of the well plate 104 are dedicated to another anti-infective. In these embodiments, one well plate 104 can comprise test wells with anywhere between two and up to 100 anti-infectives. In additional embodiments, one well plate 104 can comprise test wells with over 100 anti-infectives (depending on the size of the well plate 104).

In other embodiments, one well plate 104 can comprise only one anti-infective such that all test wells of the well plate 104 are dedicated to the one anti-infective.

The sensor array lid 102 and the well plate 104 can be made in part of a polymeric material or a thermoplastic. In some embodiments, parts of the sensor array lid 102, the well plate 104, or a combination thereof can also be made of a metallic material, a ceramic, or a combination of such materials with or without a polymeric material.

In certain embodiments, the well plate 104 can be a commercially-available or off-the-shelf well plate such as a microtiter or microwell plate distributed by ThermoFisher Scientific, Beckman Coulter, VWR International, or MilliporeSigma. As a more specific example, the well plate 104 can be a commercially-available or off-the-shelf AST well plate.

In some embodiments, the well plate 104 and parts of the sensor array lid 102 can be made in part of at least one of polystyrene, polypropylene, a cyclic olefin copolymer, or another biocompatible polymeric material.

The sensor array lid 102 can be made of a material that can withstand sterilization by radiation (e.g., gamma rays), heat, or a combination thereof. In certain embodiments, the sensor array lid 102 can be individually packaged and provided separately from the well plate 104.

In some embodiments, the sensor array lid 102 can be made to be disposable or used only one time. In these embodiments, the sensor array lid 102 can be discarded after a testing procedure has been completed.

Figure 1B:
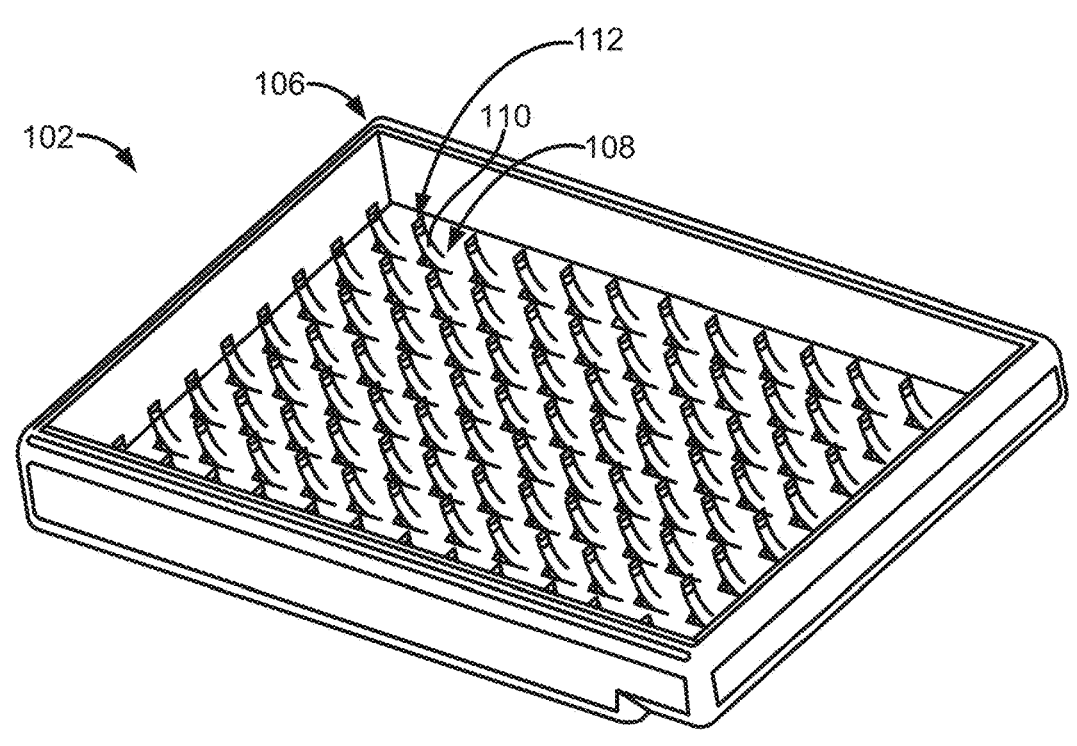
FIG. 1B illustrates a perspective view of an underside of the sensor array lid.

FIG. 1B illustrates a perspective view of an underside of the sensor array lid 102. As shown in FIGS. 1A and 1B, the sensor array lid 102 can comprise a lid top 106 and a flexible substrate 108 coupled to the underside of the lid top 106.

The flexible substrate 108 can comprise a plurality of substrate strips 110 or substrate segments partially cut out or otherwise separated from a remainder of the flexible substrate 108 (i.e., the parts of the flexible substrate 108 coupled to the underside of the sensor array lid 102). The substrate strips 110 can be curled or bent vertically downward relative to a surrounding portion of the flexible substrate 108. The substrate strips 110 can maintain its curled or bent configuration even when the sensor array lid 102 covers or caps the well plate 104.

As will be discussed in more detail in the following sections, each of the substrate strips 110 can comprise an active electrode 118 and a reference electrode 120 disposed on the substrate strip 110 (see FIG. 1H). The active electrode 118 and the reference electrode 120 can each be connected to an electrical contact pad 115 on the sensor array lid 102 by one or more conductive traces 122 (see FIG. 1H). In some embodiments, the electrical contact pad 115 can be mounted, connected, or electrically coupled to the flexible substrate 108.

For purposes of this disclosure, each of the substrate strips 110 (comprising the active electrode 118 and the reference electrode 120) can also be referred to as a sensor unit 112.

Although FIG. 1B illustrates the sensor array lid 102 as

In some embodiments, the flexible substrate 108 can be made, at least in part, of a flexible polymeric material. For example, the flexible substrate 108 can be made in part of a flexible sheet of polyethylene terephthalate (PET).

The flexible substrate 108 can also be made in part of a flexible printed circuit board (PCB) material. For example, the flexible substrate 108 can be made in part of polyimide or polyamide.

In alternative embodiments, the flexible substrate 108 can be made in part of a conductive metal substrate. For example, in these embodiments, the flexible substrate 108 can be made in part of a sheet of stainless steel foil.

In some embodiments, the flexible substrate 108 can be coupled to the underside of the lid top 106 by a biocompatible adhesive (e.g., a biocompatible polymeric adhesive, a cyanoacrylate adhesive, etc.) and a fastener (e.g., screws, clips, clasps, etc.).

FIGS. 1C-1E illustrate perspective, top, and bottom views, respectively, of one embodiment of the testing device 100 in an assembled configuration. As shown in FIGS. 1C-1E, the sensor array lid 102 can completely cover or fit over a top of the well plate 104 when the device 100 is in the assembled configuration. Moreover, as shown in FIG. 1C, the sides of the sensor array lid 102 can at least partially cover or surround the sides of the well plate 104. This can allow the device 100 to have a low-profile or compactprofile when the device 100 is in the assembled configuration such that the device 100 fits within a receiving slot 702 of the reader 700 (see FIGS. 7A, 7B, and 8).

FIGS. 1C and 1D also illustrate that the lid top 106 of the sensor array lid 102 can protect the samples within the wells 105 from contamination and prevent the samples from spilling or inadvertently leaking out.

The device 100, in the assembled configuration, can have a device length, a device width, and a device height. In some embodiments, the device 100 in the assembled configuration can have a device length of between about 80.0 mm and 160.0 mm (e.g., about 122.5 mm), a device width of between about 60.0 mm and 100.0 mm (e.g., 81.0 mm), and a device height of between about 10.0 mm and 30.0 mm (e.g., about 20.0 mm).

As will be discussed in more detail in the following sections, each of the sensor units 112 (for example, implemented as curled or bent substrate strips 110) can extend into a well 105 of the well plate 104 when the sensor array lid 102 covers or caps the well plate 104. When the wells 105 of the well plate 104 are filled with an inoculum/aliquot of the sample, at least part of the sensor unit 112 can be immersed in the inoculum/aliquot of the sample.

Figure 1F:
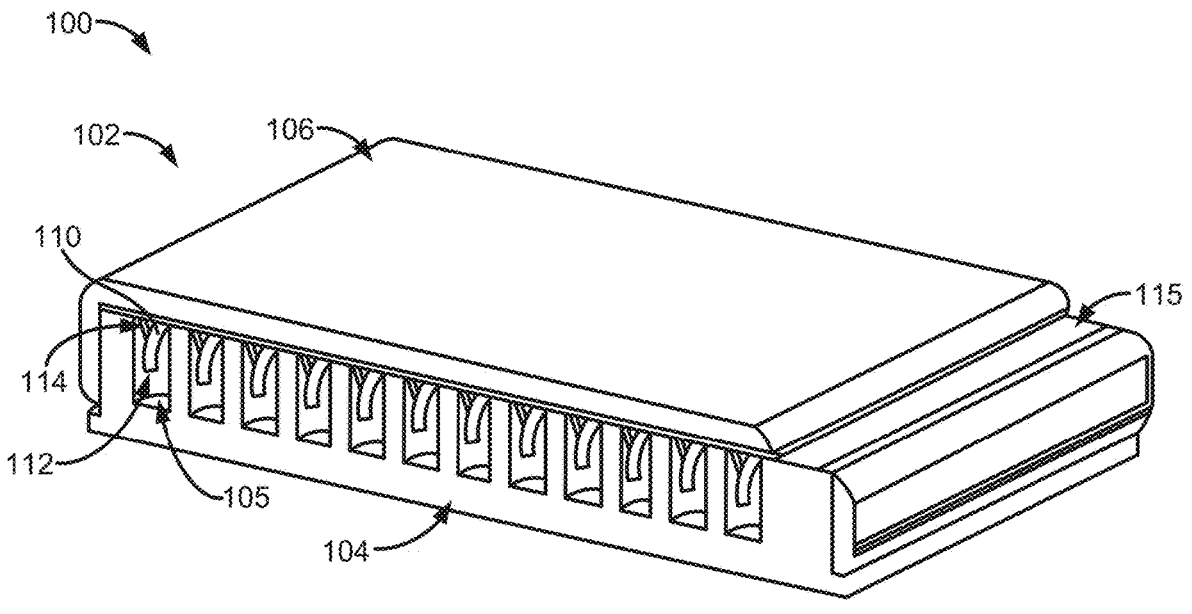
FIG. 1F illustrates a perspective view of one embodiment of the testing device in the assembled configuration where a lateral side of the device is shown as a cross-section for illustrative purposes.

FIG. 1F illustrates a perspective view of one embodiment of the testing device 100 in the assembled configuration where a lateral side of the device 100 is shown as a cross-section for illustrative purposes. In this embodiment, the sensor units 112 are implemented as curled or bent substrate strips 110 extending downward from the flexible substrate 108. As will be discussed in more detail in the following sections, each of the substrate strips 110 can comprise an active electrode 118 and a reference electrode 120 printed, deposited, or electroplated onto a distal end or distal portion of the substrate strip 110.

The substrate strips 110 can extend into the wells 105 of the well plate 104. When the wells 105 of the well plate 104 are filled with aliquots of a sample (e.g., a positive blood culture), at least a distal segment or portion of each of the substrate strips 110 (the distal segment or distal portion comprising the active electrode 118 and the reference electrode 120) can be immersed in the sample.

The sensor units 112 can be aligned to match the alignment or arrangement of the wells 105. For example, when the well plate 104 comprises 96 wells arranged as an 8×12 array of wells 105, the sensor array lid 102 can comprise 96 sensor units 112 arranged as an 8×12 array of sensor units 112.

In some embodiments the sensor units 112 can be spaced between about 6.00 mm and 12.0 mm (about 9.00 mm) apart from each other.

In certain embodiments, the sensor units 112 can be arranged in such a way that none of the sensor units 112 touch or make contact with the walls of the wells 105 when the sensor array lid 102 covers or caps the well plate 104.

In other embodiments, the sensor units 112 can be arranged in such a way that the sensor units 112 rest against or makes contact with one or more walls of the wells 105 when the sensor array lid 102 covers or caps the well plate 104.

FIG. 1F illustrates that when the sensor units 112 are implemented as substrate strips 110, the sensor array lid 102 can comprise a plurality of posts 114 extending from the underside of the lid top 106. The posts 114 can be configured to push or press against the substrate strips 110 such that the substrate strips 110 maintain their curled or bent configuration.

For example, the posts 114 can be angled to allow the posts 114 to push or press against the substrate strips 110 to ensure the substrate strips 110 maintain their curled or bent configuration. As a more specific example, the posts 114 can be positioned at an oblique angle with respect to the underside of the lid top 106.

The sensor array lid 102 can further comprise an electrical contact pad 115 disposed at one end, corner, or edge of the sensor array lid 102. In some embodiments, the electrical contact pad 115 can be mounted, connected, or electrically coupled to the flexible substrate 108.

For example, the entire electrical contact pad 115 can be left exposed by the lid top 106. As a more specific example, the electrical contact pad 115 can be located on a ledge or stepped-down portion of the sensor array lid 102.

In other embodiments, at least part of the electrical contact pad 115 can be exposed by one or more openings or apertures defined along the lid top 106.

Figure 1G:
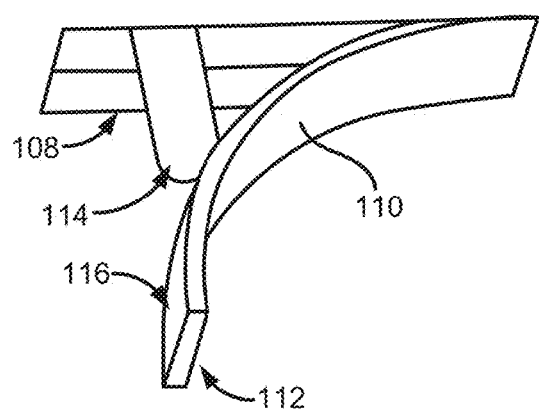
FIG. 1G is a close-up view of a post pushing against a substrate strip to allow the substrate strip to maintain a curled or bent configuration.
Figure 1H:
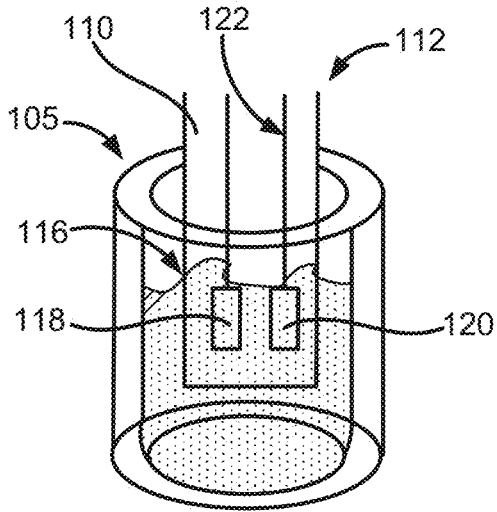
FIG. 1H is a schematic illustration showing a sensor unit comprising an active electrode and a reference electrode of the sensor unit immersed within a sample in a well of the well plate.

The contact pad 115 can be electronically connected or coupled to an active electrode 118 and a reference electrode 120 of each of the sensor units 112 by a plurality of conductive traces 122 (see, FIG. 1H). In some embodiments, the conductive traces 122 can be routed along a surface or side of the flexible substrate 108 (e.g., the side or surface adhered or coupled to the underside of the lid top 106).

In other embodiments, the conductive traces 122 can be routed or extend through the flexible substrate 108 or through a body of the lid top 106. For example, when the flexible substrate 108 is made of a PCB material, the conductive traces 122 can be routed or directed through vias or through-holes arranged along the flexible substrate 108.

The contact pad 115 can be configured to contact or otherwise engage with conductive connections within the reader 700 when the entire testing device 100 (in the assembled configuration) is inserted or introduced into a receiving slot 702 of the reader 700 to allow the reader 700 to obtain signals from the sensor units 112.

FIG. 1G is a close-up view of a post 114 pushing against a substrate strip 110 to allow the substrate strip 110 to maintain its curled or bent configuration. As shown in FIG. 1G, the post 114 can push or press against the substrate strip 110 in such a way that a distal segment 116 of the substrate strip 110 (for example, the distal segment comprising the active electrode 118 and the reference electrode 120, see FIG. 1H) is substantially perpendicular to portions of the flexible substrate 108 that are coupled to the underside of the lid top 106.

In other embodiments, the post 114 can push or press against the substrate strip 110 in such a way that the distal segment 116 of the substrate strip 110 is positioned at an oblique angle (more specifically, an angle between 60° and 90°) with respect to portions of the flexible substrate 108 that are coupled to the underside of the lid top 106.

As shown in FIG. 1G, the substrate strip 110 can be formed by cutting along the three sides surrounding the substrate strip 110.

In some embodiments, the substrate strips 110 can be substantially rectangular in shape. For example, the substrate strips 110 can be formed as rectangular tabs or rectangular strips.

In other embodiments, the substrate strips 110 can be substantially triangular, oval, or semicircular in shape. In further embodiments, the substrate strips 110 can be shaped as leaves or leaflets.

In these and other embodiments, the posts 114 can be made of the same non-conductive material (e.g., polymeric material) used to make the lid top 106.

In some embodiments, the posts 114 can be rods or pins extending from the underside of the lid top 106. In further embodiments, the posts 114 can be adhered or otherwise fastened to the lid top 106.

In certain embodiments, the posts 114 can be replaced by protuberances or other type of surface features protruding from the underside of the lid top 106.

Although the figures illustrate the substrate strips 110 being pushed or pressed into the curled or bent configuration by the posts 114, it is contemplated by this disclosure that the substrate strips 110 can also attain and maintain their curled or bent configuration without the assistance of the posts 114 (e.g., by being pre-shaped, pre-set, pre-trained, or otherwise manipulated into such a configuration).

FIG. 1H is a schematic illustration showing a sensor unit 112 of the sensor array lid 102 comprising an active electrode 118 and a reference electrode 120 of the sensor unit 112 immersed within a sample in a well 105 of the well plate 104.

The wells 105 of the well plate 104 can be sized to hold a sufficient amount of the sample to allow at least the distal segment 116 of the sensor unit 112 to be immersed in the sample when the sensor array lid 102 covers or caps the well plate 104.

As shown in FIG. 1H, each of the wells 105 of the well plate 104 can comprise a substantially cylindrical cavity for receiving and holding the sample. In other embodiments, each of the wells 105 of the well plate 104 can comprise a substantially cuboid cavity, an ovoid cavity, or a frustoconical cavity.

As previously discussed, the sensor units 112 extending from the underside of the sensor array lid 102 can be arranged or positioned such that the sensor units 112 are aligned with the wells 105 of the well plate 104 and at least the distal segment 116 of each of the sensor units 112 extend into a cavity of each of the wells 105.

When the sensor units 112 are implemented as curled or bent substrate strips 110, the distal segment 116 of the sensor unit 112 can refer to a distal segment or portion of the substrate strip 110.

As shown in FIG. 1H, the distal segment 116 of the sensor unit 112 can comprise the active electrode 118 and the reference electrode 120 disposed on the substrate strip 110. As will be discussed in more detail in the following sections, at least one of the active electrode 118 and the reference electrode 120 can be screen-printed, electroplated, or sputter deposited on the substrate strip 110.

The active electrode 118 can comprise a redox-active material. In some embodiments, the redox-active material can be a noble metal. For example the redox-active material can be platinum, gold, or a combination or alloy thereof. In other embodiments, the redox-active material can be a redox sensitive metal oxide.

In other embodiments, the redox-active material can be a conductive metal oxide such as iridium oxide, ruthenium oxide, or any combinations or alloys of such materials with noble metals. In additional embodiments, the redox-active material can be a carbon-based electrode.

The reference electrode 120 can comprise a reference electrode material. In some embodiments, the reference electrode material can comprise at least one of silver/silver chloride (Ag/AgCl) and carbon. For example, when the reference electrode material is Ag/AgCl or carbon, the reference electrode material can be screen-printed onto the substrate strip 110.

The reference electrode 120 can be considered a pseudo reference electrode since the reference electrode 120 operates without a reference buffer. A pseudo reference electrode can be used in these instances since measurements are made by comparing changes in the signal rather than comparing absolute values.

As will be discussed in more detail in later sections, the reference electrode material can be coated by an ion exchange membrane or an ionomer coating.

In alternative embodiments, the active electrode 118 can be implemented as a pin, rod, or segment of wire made of the redox-active material. In these and other embodiments, the reference electrode 120 can also be implemented as a pin, rod, or segment of wire coated or covered by the reference electrode material, the ion exchange membrane/ionomer coating, or a combination thereof.

The active electrode 118 and the reference electrode 120 can also be electrically connected to the electrical contact pad 115 on the sensor array lid 102 by a plurality of conductive traces 122. In some embodiments, the conductive traces 122 can be platinum traces or routing lines. In other embodiments, the conductive traces 122 can be made of another conductive material such as gold, copper, etc.

Figure 2A:
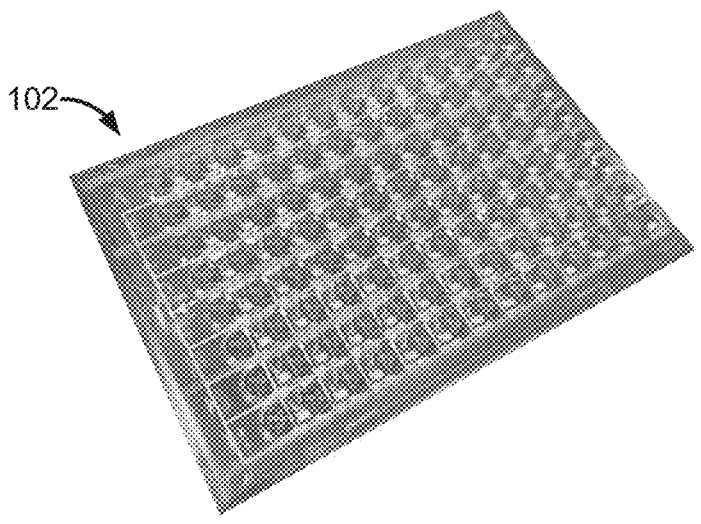
FIG. 2A is a black-and-white image showing one embodiment of the sensor array lid.

FIG. 2A is a black-and-white image showing one embodiment of the sensor array lid 102. As shown in FIG. 2A, the sensor array lid 102 can be made of a clear polymeric material to allow a medical or laboratory professional or technician to view the wells 105 of the well plate 104 and to view the samples within the wells 105 during the testing procedure. Moreover, the sensor array lid 102 can be made of a clear polymeric material to allow a medical or laboratory professional or technician to view the sensor units 112 and to ensure that the sensor units 112 are immersed in the samples within the wells 105.

As previously mentioned, in some embodiments, the sensor array lid 102 can be made in part of at least one of polystyrene, polypropylene, a cyclic olefin copolymer, or another biocompatible polymeric material.

Figure 2B:
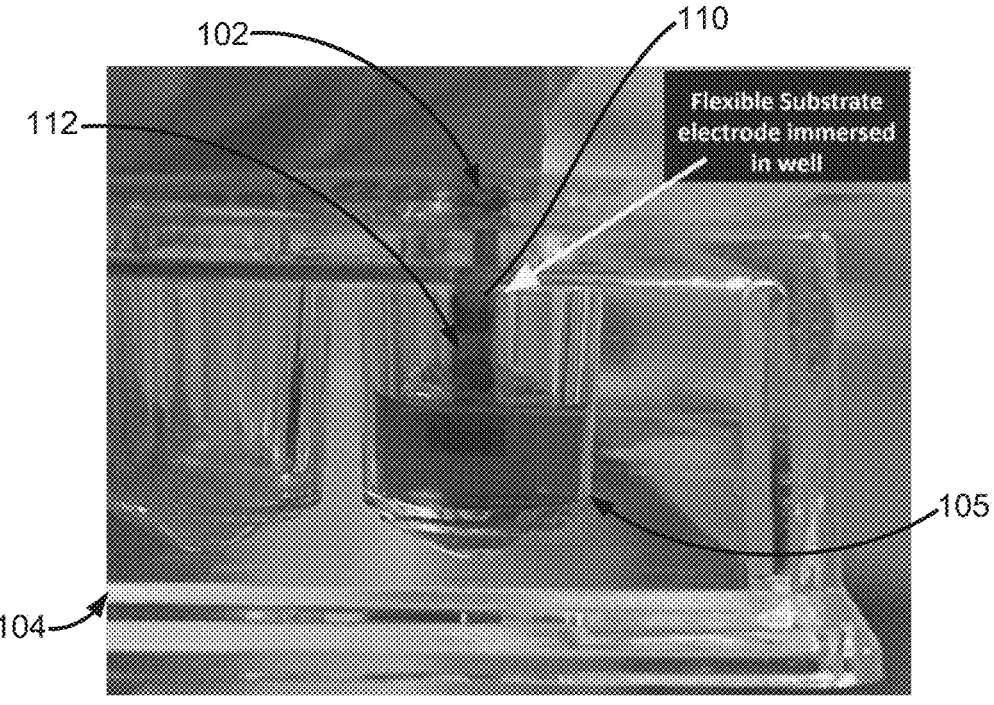
FIG. 2B is a black-and-white image showing a close-up of a sensor unit implemented as a substrate strip immersed within a sample in a well of the well plate.

FIG. 2B is a black-and-white image showing a close-up view of a sensor unit 112 implemented as a substrate strip 110 immersed within a sample in a well 105 of the well plate 104.

The sample shown in FIG. 2B is an aliquot of a positive blood culture (PBC) comprising an infectious agent. The sample can be diluted with a bacterial growth media such as Mueller Hinton broth (MHB).

Moreover, as shown in FIG. 2B, a distal portion or segment of the sensor unit 112 (implemented as a substrate strip 110) comprising the electrodes (e.g., the active electrode 118 and the reference electrode 120, see also, FIG. 1H) can be immersed in the sample when the sensor array lid 102 covers or caps onto the well plate 104.

One technical problem faced by the applicant is how to design a low-cost and accurate antimicrobial susceptibility testing device that measures multiple samples simultaneously with ease of handling. One technical solution discovered and developed by the applicant is the sensor array lid disclosed herein comprising a lid top, a flexible substrate coupled to the underside of the lid top, and strips of the flexible substrate partially cut out from the flexible substrate that serve as carriers for an active electrode and a reference electrode disposed on the substrate strips. The sensor array lid can be configured to cover a well plate (including a commercially-available well plate) comprising anywhere from between 12 wells up to 192 wells. The strips of the flexible substrate comprising the active electrode and the reference electrode can extend into the wells of the well plate and the electrodes can be immersed in samples within the wells when the sensor array lid covers the well plate. The entire testing device (the sensor array lid covering the well plate) can then be inserted (for example, as a cartridge) into a reader to determine whether the infectious agents within the samples are susceptible to the anti-infectives or antibiotics within the wells.

Figure 3A:
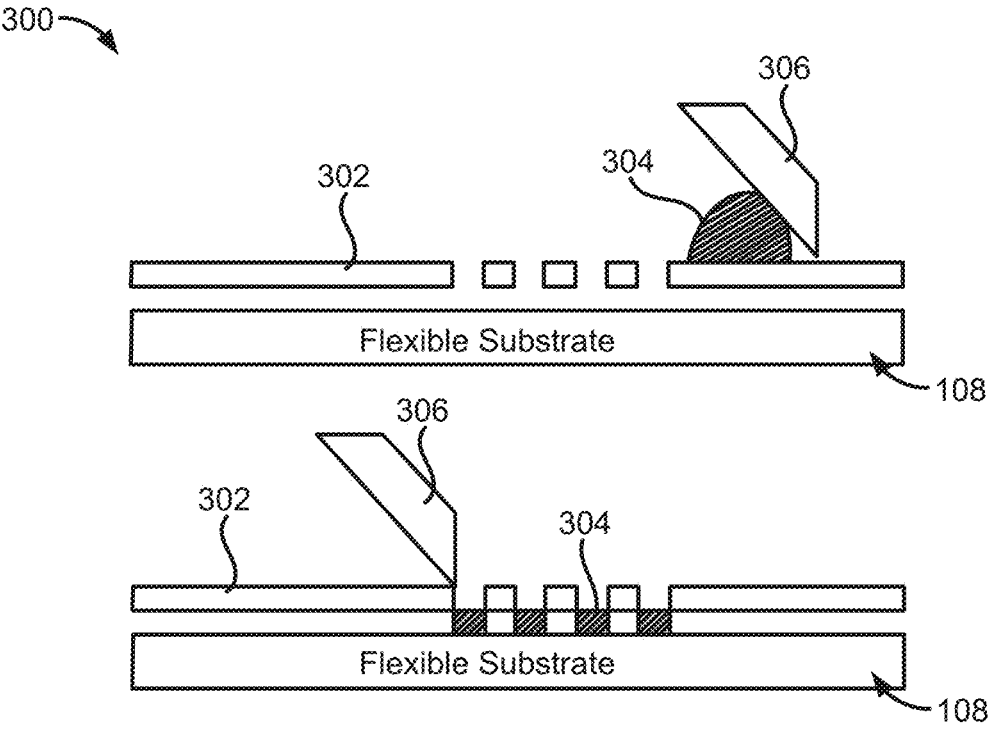
FIG. 3A illustrates a method of creating a screen-printed electrode on a flexible substrate.

FIG. 3A illustrates part of a method 300 of creating a screen-printed electrode on the flexible substrate 108. The method 300 can comprise covering the flexible substrate 108 with a stencil 302 or mesh. The stencil 302 or mesh can comprise a stencil pattern or mesh pattern. The stencil pattern or mesh pattern can match a desired layout or footprint of a material 304 (e.g., an electrode material, a coating, etc.) to be printed on the flexile substrate 108. A blade 306 (e.g., a squeegee blade) can be used to apply, transfer, or otherwise deposit the material 304 through cutouts or openings making up the stencil pattern. The blade 306 can be pushed or pulled to apply, transfer, or otherwise direct a thin layer of the material 304 onto the flexible substrate 108 in the desired shape or pattern.

The deposited material 304 can then be dried and/or cured and, in some cases, one or more solvents can be used to ensure proper adhesion of the material 304 to the flexible substrate 108. The process can be repeated until enough of the material 304 is adhered to the flexible substrate 108.

In some embodiments, the reference electrode material of the reference electrode 120 can be screen-printed onto the flexible substrate 108. In these and other embodiments, the redox-active material of the active electrode 118 can also be screen-printed onto the flexible substrate 108.

In additional embodiments, an ion exchange membrane 308 or an ionomer coating can also be screen-printed onto at least part of the flexible substrate 108. For example, as will be discussed in more detail in the following sections, the ion exchange membrane 308 or the ionomer coating can be screen-printed onto a reference electrode material (e.g., Ag/AgCl or carbon/graphite) that has already been screen-printed onto the flexible substrate 108.

As previously discussed, in some embodiments, the redox-active material can be a noble metal such as platinum, gold, or a combination or alloy thereof. In these embodiments, the redox-active material can initially take the form of an ink or paste (e.g., platinum or gold ink or paste). The ink or paste (e.g., platinum or gold ink or paste) can be screen-printed onto the flexible substrate 108 using the method previously disclosed (e.g., method 300).

In other embodiments, the redox-active material can be a conductive metal oxide such as iridium oxide, ruthenium oxide, or any combinations or alloys of such materials with noble metals. In additional embodiments, the redox-active material can be a carbon-based electrode.

Also, as previously discussed, the reference electrode material can comprise at least one of silver/silver chloride (Ag/AgCl) and carbon. In these embodiments, the reference electrode material can also initially take the form of an ink or paste (e.g., silver/silver chloride or graphite ink or paste). This ink or paste (e.g., silver/silver chloride or graphite ink or paste) can be screen-printed onto another portion of the flexible substrate 108.

For example, the redox-active material can be screen-printed onto a distal segment 116 of a substrate strip 110. In this example, the reference electrode material can be screen-printed onto this same distal segment 116 of the substrate strip 110 but next to or in proximity to the redox-active material.

In alternative embodiments, the Ag/AgCl reference electrode material can also be made by chlorinating silver with electrical current flow in a chlorinated solution.

Figure 3B:
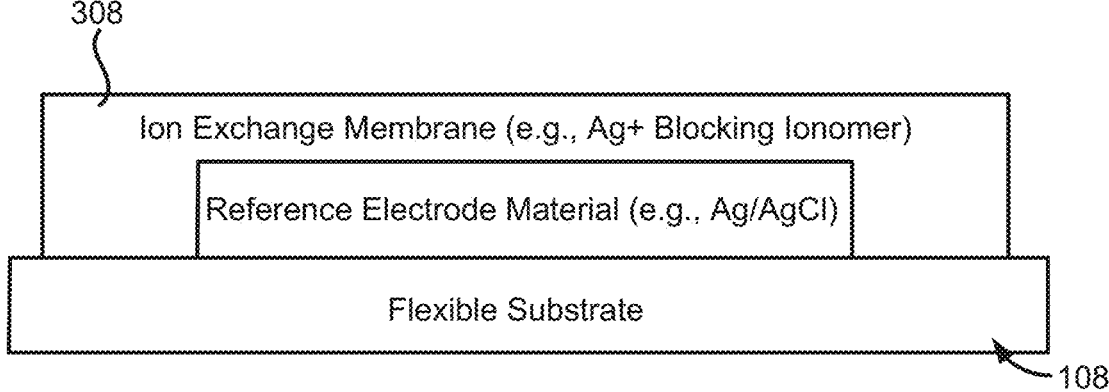
FIG. 3B is a schematic diagram illustrating part a reference electrode material disposed on a flexible substrate and the reference electrode material covered entirely by an ion exchange membrane.

FIG. 3B is a schematic diagram illustrating a reference electrode material disposed on the flexible substrate 108 and the reference electrode material covered entirely by an ion exchange membrane 308.

In some embodiments, the ion exchange membrane 308 can be an ionomer coating capable of blocking certain ions (e.g., Ag⁺ ions) that can interact with or adversely affect certain microbial organisms or other infectious agents. For example, the ion exchange membrane 308 can be a sulfonated tetrafluoroethylene based fluoropolymer-copolymer such as Nafion™. The sulfonated tetrafluoroethylene based fluoropolymer-copolymer can also be referred to as a proton exchange membrane since it can be designed to only allow positively charged ions (e.g., H⁺ ions) to freely flow through its polymer layer but can slow the diffusion or flow of other ions (e.g., Ag⁺ ions) that may interact with or be harmful to certain microbial organisms or other infectious agents, keeping such ions close to the reference electrode material.

In other embodiments, the ion exchange membrane 308 can be a polyaromatic polymer anion exchange membrane such as Fumion™. The a polyaromatic polymer anion exchange membrane can be designed to only allow anions to pass through its polymer layer. Since certain harmful ions such as Ag⁺ ions are cations, such ions are blocked from entering the sample.

In some embodiments, the ion exchange membrane 308 can be screen-printed onto the flexible substrate 108 and onto the reference electrode material disposed on the flexible substrate 108. In certain embodiments, the reference electrode material can first be screen printed onto the flexible substrate 108 and the ion exchange membrane 308 can be subsequently screen printed onto the reference electrode material and part of the flexible substrate 108.

One technical problem faced by the applicant is how to prevent harmful ions on the electrode from entering into the sample and adversely affecting the growth and metabolism of the infectious agents. One technical solution discovered and developed by the applicant is to screen-print an ion exchange membrane over an7 parts of the electrode (e.g., the reference electrode) that might shed such interfering or harmful ions.

In alternative embodiments, at least one of the active electrode 118 and the reference electrode 120 can be formed via sputter deposition. For example, at least one of the redox-active material of the active electrode 118 (e.g., platinum) and the reference electrode material of the reference electrode 120 can be sputter deposited onto the flexible substrate 108 to form such electrodes. As will be discussed in more detail in relation to FIG. 5, the performance of sensor units 112 comprising electrodes formed via sputter deposition were compared against a commercially-available ORP sensor, such sputter-deposited sensors produced results comparable to the commercially-available ORP sensor.

In alternative embodiments, at least one of the active electrode 118 and the reference electrode 120 can be formed via electroplating. For example, at least one of the redox-active material of the active electrode 118 (e.g., platinum and/or gold) and the reference electrode material of the reference electrode 120 can be electroplated onto the flexible substrate 108 to form such electrodes. As a more specific example, when the flexible substrate 108 is made of a flexible PCB material (e.g., polyimide/polyamide), at least one of the redox-active material of the active electrode 118 (e.g., platinum and/or gold) and the reference electrode material of the reference electrode 120 can be electroplated onto the flexible PCB material. As will be discussed in more detail in relation to FIG. 6, the performance of two sensor units 112 comprising electrodes formed via electroplating were compared against one another to determine the precision of such sensors.

FIG. 4A illustrates an ORP bacterial growth curve of a sample comprising *E. coli* (e.g., the ATCC-25922 strain of *E. coli*) obtained using an embodiment of the testing device 100 with screen-printed platinum active electrodes 118 and screen-printed carbon reference electrodes 120. Also shown is an ORP bacterial growth curve obtained using a commercially available ORP sensor. The sample can be diluted using a Mueller Hinton broth as the dilutive solution prior to being introduced into the wells 105 of the well plate 104. The commercially-available ORP sensor was an ORP sensor distributed by Mettler Toledo.

As shown in FIG. 4A, the ORP growth curve obtained using the testing device 100 comprising screen-printed platinum active electrodes 118 and screen-printed carbon reference electrodes 120 performed comparable to the commercially-available ORP sensor.

FIG. 4B illustrate various ORP bacterial growth curves showing the growth behavior of susceptible and resistant bacteria in both test wells comprising an anti-infective and control wells devoid of any anti-infective. Also shown is an ORP bacterial growth curve obtained using a commercially available ORP sensor.

The anti-infective used was ceftriaxone. The ceftriaxone was only present in test wells while the control wells contained no anti-infectives. The susceptible bacteria used was the CDC-650 strain of *E. coli*, which is know to be highly susceptible to ceftriaxone. The resistant bacteria used for was the CDC-846 strain of *E. coli*, which is known to be resistant to ceftriaxone. The commercially-available ORP sensor was an ORP sensor distributed by Mettler Toledo.

Samples comprising both the susceptible and resistant bacteria were first diluted using a Mueller Hinton broth as the dilutive solution and then introduced to both test wells and control wells of the well plate 104. A sensor array lid 102 with substrate strips 110 comprising screen-printed platinum active electrodes 118 and screen-printed carbon reference electrodes 120 served as the sensor units 112. All samples were incubated at 37° C.

As shown in FIG. 4B, the ORP growth curves obtained using the testing device 100 comprising the screen-printed platinum active electrodes 118 and the screen-printed carbon reference electrodes 120 performed as expected and the ORP growth curves obtained using the device 100 were comparable to the ORP growth curves obtained using the commercially-available ORP sensor.

Figure 5:
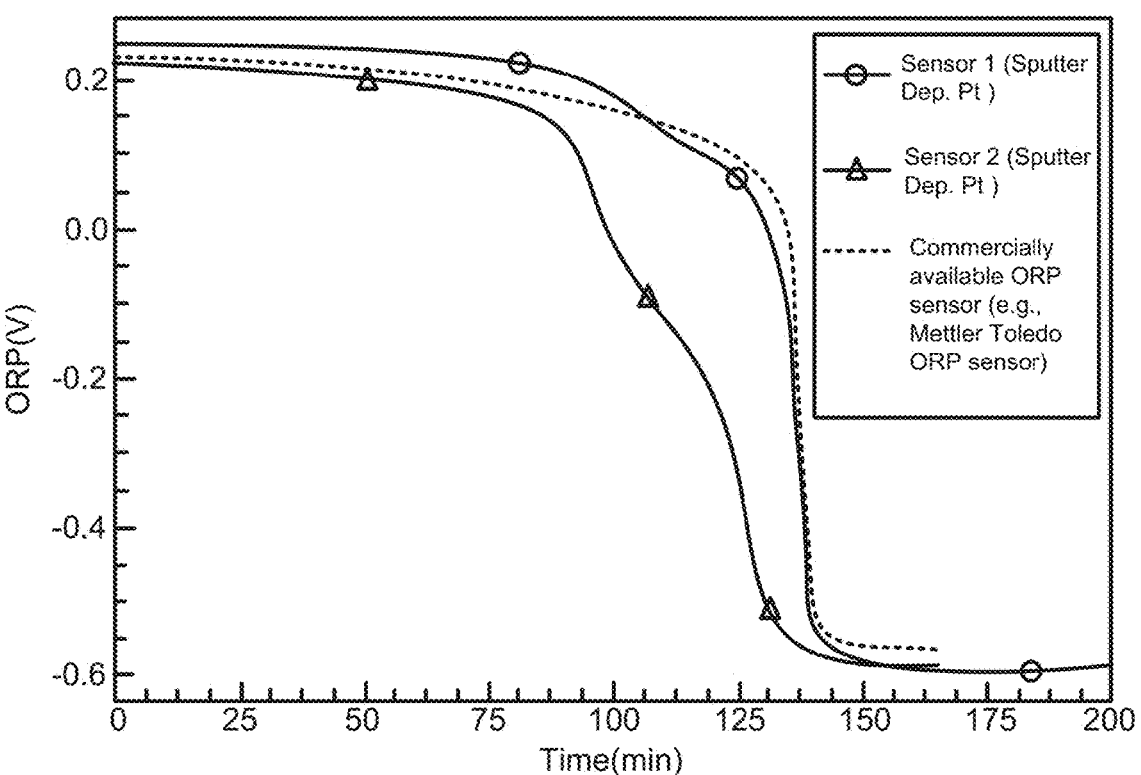
FIG. 5 illustrates ORP bacterial growth curves obtained using an embodiment of the testing device with sputter deposited electrodes. Also shown is an ORP bacterial growth curve obtained using a commercially available ORP sensor.

FIG. 5 illustrates ORP bacterial growth curves obtained using an embodiment of the testing device 100 with sensor units 112 comprising sputter deposited platinum active electrodes 118. Also shown is an ORP bacterial growth curve obtained using the commercially available Mettler Toledo ORP sensor.

As shown in FIG. 5, the ORP growth curves obtained using the testing device 100 with sensor units 112 comprising the sputter deposited platinum active electrodes 118 were comparable to the ORP growth curve obtained using the commercially-available ORP sensor.

Figure 6:
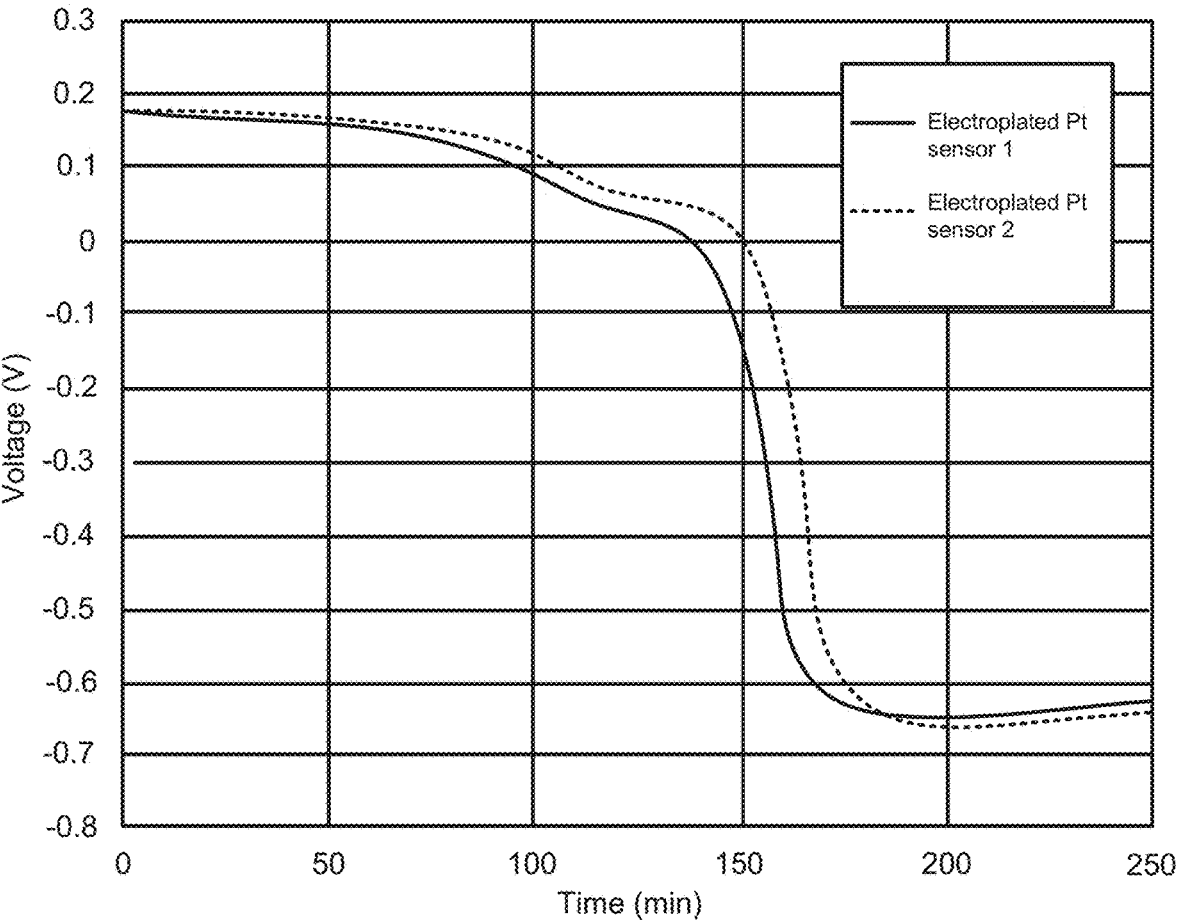
FIG. 6 illustrates ORP bacterial growth curves obtained using an embodiment of the testing device with electroplated electrodes.

FIG. 6 illustrates ORP bacterial growth curves obtained using an embodiment of the testing device 100 with sensor units 112 comprising electroplated platinum active electrodes 118. The platinum active electrodes 118 were electroplated on a flexible substrate 108 made of a flexible PCB material.

As shown in FIG. 6, the ORP growth curves obtained using the testing device 100 with sensor units 112 comprising electroplated platinum active electrodes 118 were comparable to one another and is an indication of the precision of the sensor units 112.

Figure 7A:
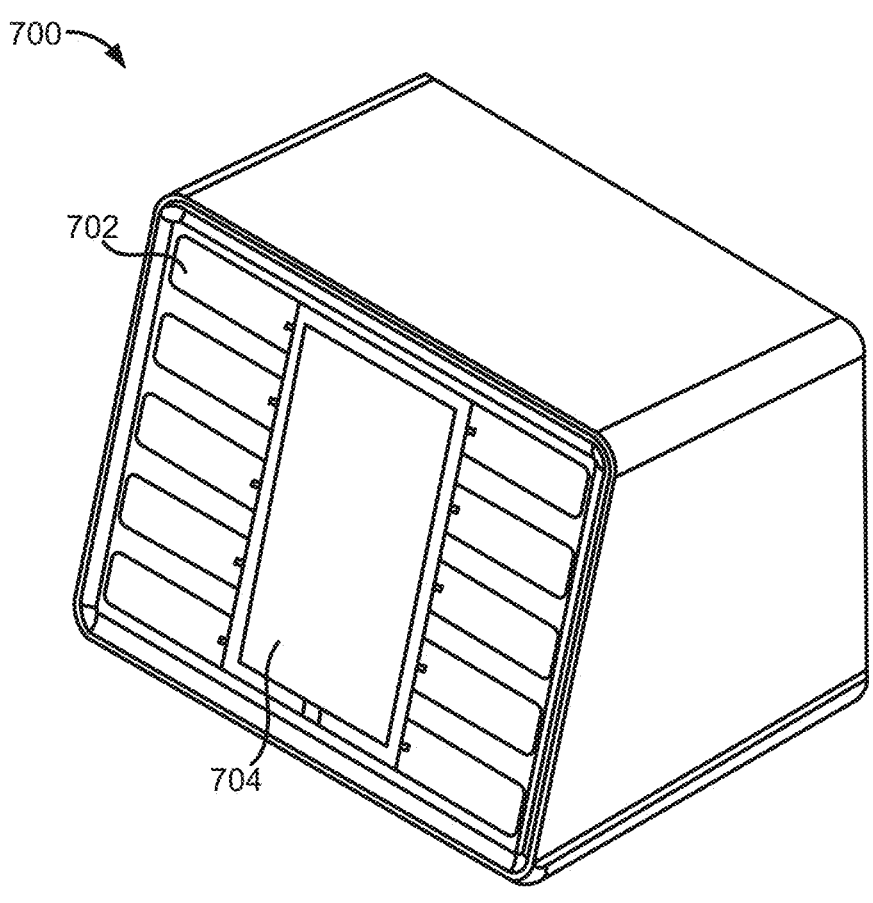
FIGS. 7A and 7B illustrate perspective and front views, respectively, of a reader for receiving the testing device and detecting changes in the solution characteristics of samples within the wells of the testing device.
Figure 7B:
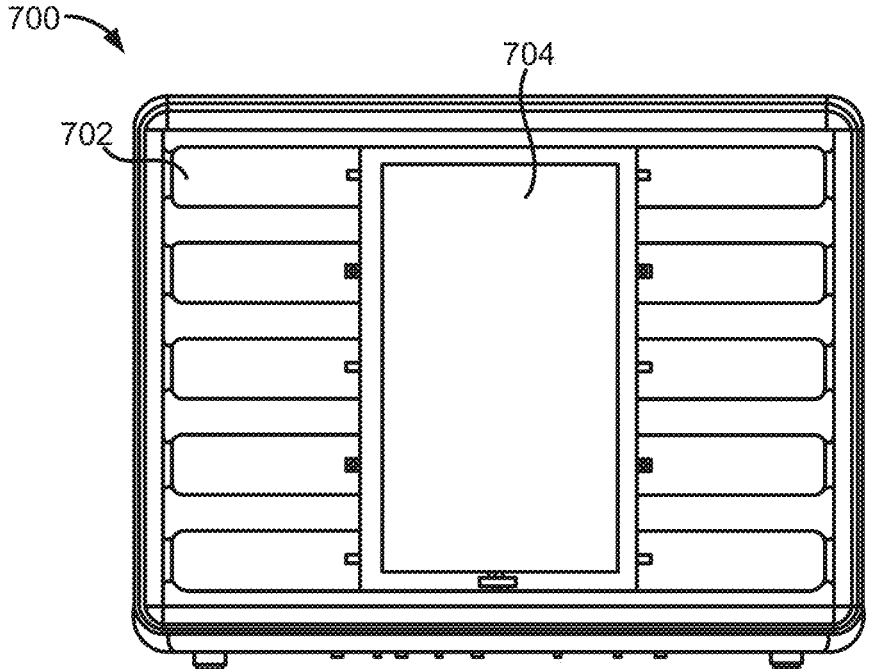

FIGS. 7A and 7B illustrate perspective and front views, respectively, of a reader 700 for receiving the testing device 100 (the well plate 104 covered by the sensor array lid 102) and detecting any changes in the solution characteristic of samples within the wells 105 of the testing device 100.

The reader 700 can comprise a plurality of receiving slots 702 for receiving and holding the testing devices 100. In some embodiments, the reader 700 can comprise between four and twelve receiving slots 702 (e.g., ten receiving slots 702).

Each of the receiving slots 702 can accommodate a testing device 100 (the well plate 104 covered by the sensor array lid 102). In certain embodiments, the testing device 100 can be placed within a cartridge prior to being inserted into the receiving slot 702.

As previously discussed, the sensor array lid 102 of the testing device 100 can further comprise an electrical contact pad 115 positioned at one end, corner, or edge of the sensor array lid 102. In some embodiments, the electrical contact pad 115 can be mounted, connected, or electrically coupled to the flexible substrate 108.

For example, the entire electrical contact pad 115 can be left exposed by the lid top 106. As a more specific example, the electrical contact pad 115 can be located on a ledge or stepped-down portion of the sensor array lid 102.

In other embodiments, at least part of the electrical contact pad 115 can be exposed by one or more openings or apertures defined along the lid top 106.

The active electrodes 118 and the reference electrodes 120 of the sensor array lid 102 can be electrically connected to the electrical contact pad 115 via conductive traces 122. The conductive traces 122 can be routed along one side of the flexible substrate 108 or along both sides of the flexible substrate 108. In certain embodiments, the conductive traces 122 can be routed through the body of the flexible substrate 108 and along one side or both sides of the lid top 106.

In some embodiments, all of the reference electrodes 120 of the sensor array lid 102 can be connected by one conductive trace 122. In other embodiments, the electrodes 120 of the sensor array lid 102 can be connected by multiple conductive traces 122.

The contact pad 115 can be configured to contact or otherwise engage with conductive connections or conductive contacts within the reader 700 when the testing device 100 (in the assembled configuration) is inserted or introduced into the receiving slot 702 (e.g., via a cartridge) of the reader 700. For example, the conductive connections within the reader 700 can engage or otherwise contact the electrical contact pad 115 of the testing device 100 when the testing device 100 (the well plate 104 covered by the sensor array lid 102) is pushed, inserted, or otherwise introduced into the receiving slot 702.

The reader 700 can automatically begin to read signals from the sensor units 112 of the sensor array lid 102 once the testing device 100 is inserted into the reader 700 via the receiving slot 702. The reader 700 can be configured to read signals from the sensor units 112 in order to detect changes in the solution characteristic of microbial samples within the wells 105 over time. The reader 700 can also be configured to determine the susceptibility of the microbes within the samples to certain anti-infectives.

The reader 700 can also comprise certain thermal circuitry and heating blocks that can be used to incubate the samples within the wells 105 of the testing device 100. For example, the testing device 100 comprising aliquots of the sample can be incubated at an incubation temperature between about 30° C. and about 40° C. In alternative embodiments, the testing device 100 comprising aliquots of the sample can be incubated outside of the reader 700.

As shown in FIGS. 7A and 7B, the reader 700 can also comprise a display 704. In some embodiments, the display 703 can be an interactive touchscreen display. The display 704 can render graphics, messages or other types of text, or a combination thereof concerning the results of the antimicrobial susceptibility test. In certain embodiments, the display 703 can allow a user to input commands to the reader 700 concerning an upcoming test, an ongoing test, or a completed test.

Figure 7C:
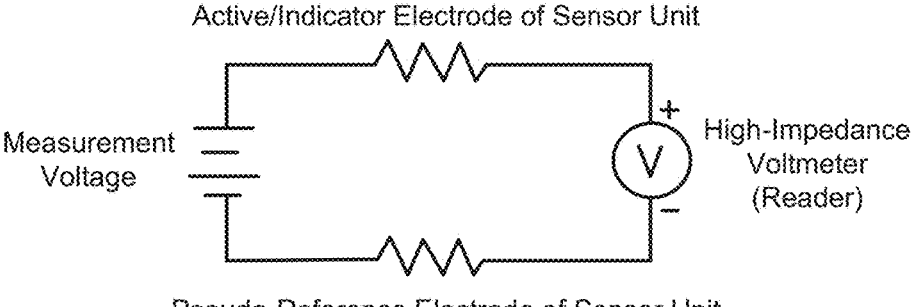
FIG. 7C illustrates a high-level circuit diagram showing how the reader reads the electrodes (active electrode and reference electrode) of the sensor unit.
Figure 7D:
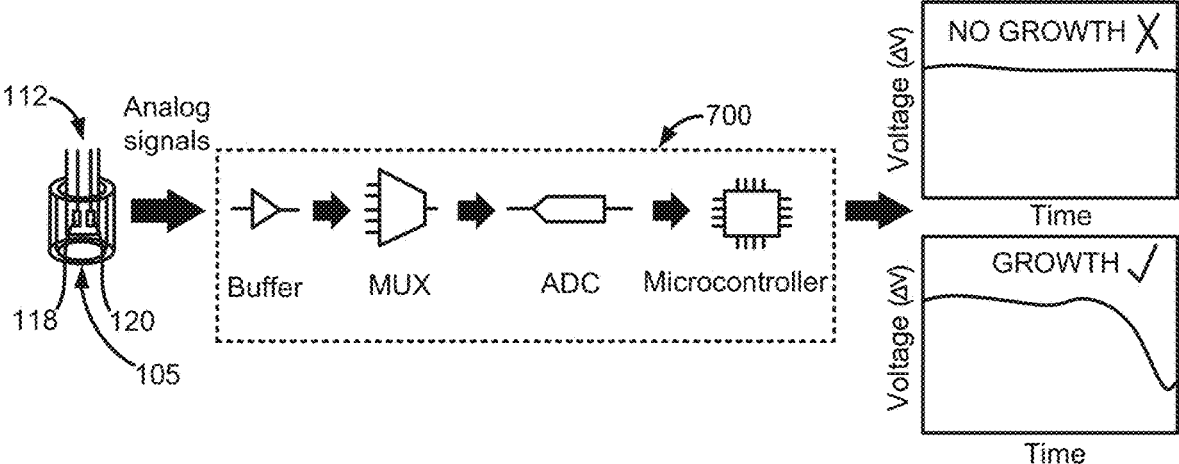
FIG. 7D is a schematic illustration showing a sensor unit extending into a well of the well plate and the components involved in processing the signals in multiple wells.

FIG. 7C illustrates a high-level circuit diagram showing how the reader 700 reads the electrodes (active electrode 118 and reference electrode 120) of the sensor unit 112 (see, also, FIGS. 1H and 7D). The reader 700 can act as a high-impedance voltmeter to measure a potential difference between the indicator or active electrode 118 of a sensor unit 112 immersed in a sample and the reference electrode 120 or pseudo reference electrode of the sensor unit 112 immersed in the same sample.

The oxidation reduction potential (ORP) of a sample can refer to the proportion of oxidized molecules to reduced molecules in the sample and is an effective metric for monitoring for infectious agent growth and metabolism (or lack thereof). Oxygen and other electron donors are consumed when infectious agents grow and metabolize. This results in a higher proportion of reduced molecules and hence a more negative ORP.

In order to measure the ORP of the medium, a redox-sensitive but inert electrode material (e.g., made of a noble metal such as platinum or gold) can be used as the active electrode 118. The reference electrode 120 can be a silver/silver chloride pseudo reference electrode or a carbon reference electrode. The reference electrode 120 does not respond to redox changes in the sample, whereas reduced molecules (molecules with an excess of electrons) readily give up electrons at the active electrode 118, resulting in a build-up of negative charges. Therefore, as infectious agent growth/metabolism progresses, the ORP in the sample becomes more negative. In the case of no infectious agent growth/metabolism, the ORP of the sample stays constant for the duration of the measurement.

FIG. 7D is a schematic diagram illustrating certain steps undertaken by electronic components of the reader 700 when processing signals obtained from the sensor units 112. As shown in FIG. 7D, analog signals read from each of the sensor units 112 can first be buffered by a buffering circuit within the reader 700. The buffered signal can then be provided as inputs to an analog multiplexer (MUX) within the reader 700. The analog multiplexer can iterate over each sensor unit 112. The analog signals from the multiplexer can then be converted to digital signals and the digital signals can be analyzed by a microcontroller within the reader 700 to determine whether the infectious agent is resistant (showing signs of growth) or susceptible (showing no signs of growth).

Figure 8:
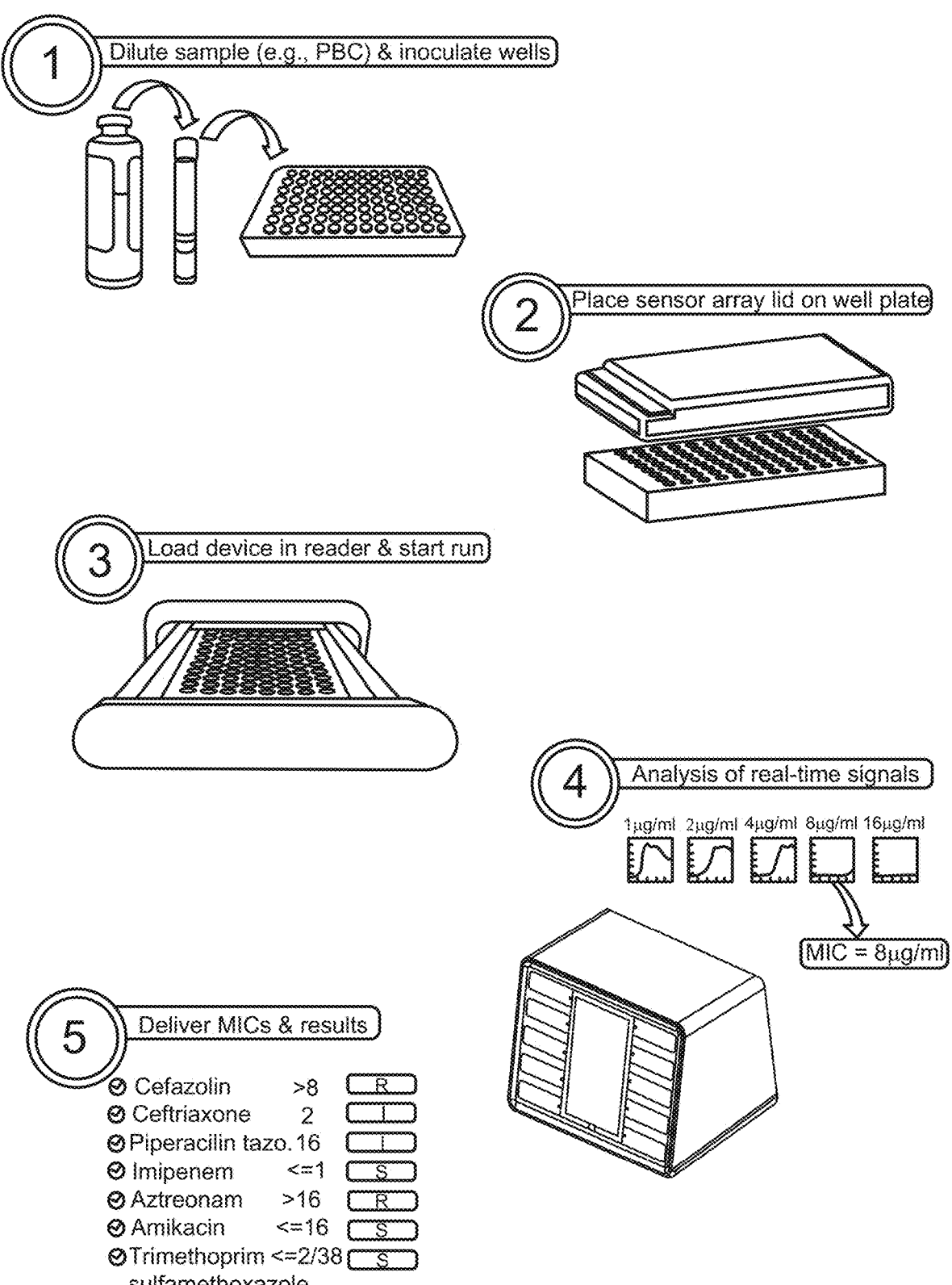
FIG. 8 illustrates various steps for determining a susceptibility of an infectious agent to an anti-infective.

FIG. 8 illustrates various steps of one embodiment of a method for determining a susceptibility of an infectious agent to an anti-infective. The method can utilize devices, apparatus, and systems disclosed herein including the testing device 100 comprising the sensor array lid 102 and the reader 700.

The method can comprise diluting a sample with a dilutive solution to a dilution ratio of between about 1:1 to about 1:10000.

In some embodiments, the sample can be obtained from a subject or patient. In other embodiments, the sample can be a biological sample, an environmental sample, or a food sample.

When the sample is an environmental sample, the sample can be obtained from a stream, river, lake, ocean, contamination site, quarantine zone, an emergency area, or some combination thereof.

When the sample is a food sample, the sample can be obtained from a food preparation facility, a dining establishment, a waste facility, or a combination thereof.

When the sample is obtained from a patient or subject, the sample can comprise at least one of a bodily fluid of the subject or patient or a re-suspended swab obtained from the subject or patient.

In some embodiments, the subject or patient can be a human subject or patient.

In other embodiments, the subject or patient can be a non-human animal subject or patient.

In some embodiments, the sample can comprise blood, urine, serum, plasma, saliva, sputum, semen, breast milk, joint fluid, spinal fluid such as cerebrospinal fluid, wound discharge, mucus, fluid accompanying stool, vaginal secretions, synovial fluid, pleural fluid, peritoneal fluid, pericardial fluid, amniotic fluid, or a combination thereof.

In some embodiments, the sample can comprise or refer to a bacterial culture derived from at least one of sample obtained from a subject or patient, a biological sample, an environmental sample, and a food sample. For example, the sample can comprise or refer to a bacterial culture or a re-suspended bacterial culture derived from a bodily fluid or swab obtained from a subject or patient.

As a more specific example, the sample can comprise or refer to a bacterial culture derived from blood or other bodily fluid obtained from a patient or subject that has tested positive for microbial growth. When the sample is a bacterial culture derived from blood, the sample can be or be referred to as a positive blood culture (PBC).

A PBC can be a bacterial culture derived from blood drawn from a subject or patient that has tested positive for bacterial growth. For example, a patient can show symptoms of sepsis (e.g., high fever, chills, etc.) and blood (e.g., 5 mL to 10 mL) can be drawn from the patient and transferred to a commercial blood culturing container or vessel that contain bacterial growth media (e.g., 30 mL to 40 mL of growth media). The blood culturing container or vessel can then be incubated at 35° C.±2° C. to allow the bacteria to proliferate. If the patient's blood is contaminated with bacteria, the bacteria will replicate within the container/vessel and a blood culturing system or apparatus can determine the sample as testing "positive" for bacterial growth. Depending on the pathogen type and growth rate, the blood culture can turn positive between 7 hours and 3 days. Such a PBC can then be used for further downstream testing (e.g., antimicrobial susceptibility testing) using the apparatus, devices, systems, and method disclosed herein.

In some embodiments, the sample can comprise bacteria. In these embodiments, the bacteria can be of a genera selected from the group consisting of: *Acinetobacter, Acetobacter, Actinomyces, Aerococcus, Aeromonas, Agrobacterium, Anaplasma, Azorhizobium, Azotobacter, Bacillus,*

*Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia,* and *Yersinia.*

More specifically, the bacteria can be of a species selected from the group consisting of: *Acinetobacter baumannii* (A. Baumannii), *Actinobacillus* spp., Actinomycetes, *Actinomyces* spp. (including but not limited to *Actinomyces israelii* and *Actinomyces naeslundii*), *Aeromonas* spp. (including but not limited to *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis,* and *Bacillus stearothermophilus*), *Bacteroides* spp. (including but not limited to *Bacteroides fragilis*), *Bartonella* spp. (including but not limited to *Bartonella bacilliformis* and *Bartonella henselae, Bifidobacterium* spp., *Bordetella* spp. (including but not limited to *Bordetella pertussis, Bordetella parapertussis,* and *Bordetella bronchiseptica*), *Borrelia* spp. (including but not limited to *Borrelia recurrentis,* and *Borrelia burgdorferi*), *Brucella* spp. (including but not limited to *Brucella abortus, Brucella canis, Brucella melintensis* and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp., *Coxiella burnetii, Corynebacterium* spp. (including but not limited to, *Corynebacterium diphtheriae, Corynebacterium jeikeum* and *Corynebacterium*), *Clostridium* spp. (including but not limited to *Clostridium perfringens, Clostridium difficile, Clostridium botulinum* and *Clostridium tetani*), *Eikenella corrodens, Enterobacter* spp. (including but not limited to *Enterobacter aerogenes, Enterobacter agglomerans, Enterobacter cloacae* and *Escherichia coli,* including opportunistic *Escherichia coli* (*E. coli*), including but not limited to enterotoxigenic *E. coli,* enteroinvasive *E. coli,* enteropathogenic *E. coli,* enterohemorrhagic *E. coli,* enteroaggregative *E. coli* and uropathogenic *E. coli*), *Enterococcus* spp. (including but not limited to *Enterococcus faecalis* and *Enterococcus faecium*), *Ehrlichia* spp. (including but not limited to *Ehrlichia chafeensia* and *Ehrlichia canis*), Erysipelothrix rhusiopathiae, *Eubacterium* spp., *Francisella tularensis, Fusobacterium nucleatum, Gardnerella vaginalis, Gemella morbillorum, Haemophilus* spp. (including but not limited to *Haemophilus influenzae, Haemophilus ducreyi, Haemophilus aegyptius, Haemophilus parainfluenzae, Haemophilus haemolyticus* and *Haemophilus parahaemolyticus, Helicobacter* spp. (including but not limited to *Helicobacter pylori, Helicobacter cinaedi* and *Helicobacter fennelliae*), *Kingella kingii, Klebsiella* spp. (including but not limited to *Klebsiella pneumoniae, Klebsiella granulo-*

*matis* and *Klebsiella oxytoca*), *Lactobacillus* spp., *Listeria monocytogenes, Leptospira interrogans, Legionella pneumophila, Leptospira interrogans, Peptostreptococcus* spp., *Moraxella catarrhalis, Morganella* spp., *Mobiluncus* spp., *Micrococcus* spp., *Mycobacterium* spp. (including but not limited to *Mycobacterium leprae, Mycobacterium tuberculosis, Mycobacterium intracellulare, Mycobacterium avium, Mycobacterium bovis*, and *Mycobacterium marinum*), *Mycoplasm* spp. (including but not limited to *Mycoplasma pneumoniae, Mycoplasma hominis*, and *Mycoplasma genitalium*), *Nocardia* spp. (including but not limited to *Nocardia asteroides, Nocardia cyriacigeorgica* and *Nocardia brasiliensis*), *Neisseria* spp. (including but not limited to *Neisseria gonorrhoeae* and *Neisseria meningitidis*), *Pasteurella multocida, Plesiomonas shigelloides, Prevotella* spp., *Porphyromonas* spp., *Prevotella melaninogenica, Proteus* spp. (including but not limited to *Proteus vulgaris* and *Proteus mirabilis*), *Providencia* spp. (including but not limited to *Providencia alcalifaciens, Providencia rettgeri* and *Providencia stuartii*), *Pseudomonas aeruginosa (P. aeruginosa), Propionibacterium acnes, Rhodococcus equi, Rickettsia* spp. (including but not limited to *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* spp., *Stenotrophomonas maltophilia, Salmonella* spp. (including but not limited to *Salmonella enterica, Salmonella typhi, Salmonella paratyphi, Salmonella enteritidis, Salmonella cholerasuis* and *Salmonella typhimurium*), *Serratia* spp. (including but not limited to *Serratia marcesans (S. marcesans)* and *Serratia liquifaciens*), *Shigella* spp. (including but not limited to *Shigella dysenteriae, Shigella flexneri, Shigella boydii* and *Shigella sonnei*), *Staphylococcus* spp. (including but not limited to *Staphylococcus aureus, Staphylococcus epidermidis, Staphylococcus hemolyticus, Staphylococcus saprophyticus*), *Streptococcus* spp. (including but not limited to *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A Streptococci, *Streptococcus pyogenes*, Group B Streptococci, *Streptococcus agalactiae*, Group C Streptococci, *Streptococcus anginosus, Streptococcus equismilis*, Group D Streptococci, *Streptococcus bovis*, Group F Streptococci, *Streptococcus anginosus*, and Group G Streptococci), Spirillum minus, *Streptobacillus moniliformi, Treponema* spp. (including but not limited to *Treponema carateum, Treponema petenue, Treponema pallidum* and *Treponema endemicum, Tropheryma whippelii, Ureaplasma urealyticum, Veillonella* spp., *Vibrio* spp. (including but not limited to *Vibrio cholerae, Vibrio parahemolyticus, Vibrio vulnificus, Vibrio parahaemolyticus,*

*Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Xanthomonas maltophilia*, and *Yersinia* spp. (including but not limited to *Yersinia enterocolitica, Yersinia pestis*, and *Yersinia pseudotuberculosis*).

In embodiments where the sample comprises bacteria, the anti-infective can comprise or be a bacteriostatic anti-infective, a bactericidal anti-infective, or a combination thereof In certain embodiments, the bacteriostatic anti-infective can comprise β-lactams (including but not limited to penicillins such as ampicillin, amoxicillin, flucloxacillin, penicillin, amoxicillin/clavulanate, and ticarcillin/clavulanate and monobactams such as aztreonam), β-lactam and β-lactam inhibitor combinations (including but not limited to piperacillin-tazobactam and ampicillin-sulbactam), Aminoglycosides (including but not limited to amikacin, gentamicin, kanamycin, neomycin, netilmicin, paromomycin, streptomycin, spectinomycin, and tobramycin), Ansamycins (including but not limited to rifaximin), Carbapenems (including but not limited to ertapenem, doripenem, imipenem, and meropenem), Cephalosporins (including but not limited to ceftaroline, cefepime, ceftazidime, ceftriaxone, cefadroxil, cefalotin, cefazolin, cephalexin, cefaclor, cefprozil, cefuroxime, cefixime, cefdinir, cefditoren, cefotaxime, cefpodoxime, ceftibuten, and ceftobiprole), Chloramphenicols, Glycopeptides (including but not limited to vancomycin, teicoplanin, telavancin, dalbavancin, and oritavancin), Folate Synthesis Inhibitors (including but not limited to trimethoprim-sulfamethoxazole), Fluoroquinolones (including but not limited to ciprofloxacin), Lincosamides (including but not limited to clindamycin, lincomycin, azithromycin, clarithromycin, dirithromycin, roxithromycin, telithromycin, and spiramycin), Lincosamines, Lipopeptides, Macrolides (including but not limited to erythromycin), Monobactams, Nitrofurans (including but not limited to furazolidone and nitrofurantoin), Oxazolidinones (including but not limited to linezolid, posizolid, radezolid, and torezolid), Quinolones (including but not limited to enoxacin, gatifloxacin, gemifloxacin, levofloxacin, lomefloxacin, moxifloxacin, naldixic acid, norfloxacin, trovafloxacin, grepafloxacin, sparfloxacin, and temafloxacin), Rifampins, Streptogramins, Sulfonamides (including but not limited to mafenide, sulfacetamide, sulfadiazine, sulfadimethoxine, sulfamethizole, sulfamethoxazole, sulfasalazine, and sulfisoxazole), Tetracyclines (including but not limited to oxycycline, minocycline, demeclocycline, doxycycline, oxytetracycline, and tetracycline), polypeptides (including but not limited to bacitracin, polymyxin B, colistin, and cyclic lipopeptides such as daptomycin), phages, or a combination or derivative thereof.

In other embodiments, the anti-infective can comprise clofazimine, ethambutol, isoniazid, rifampicin, arsphenamine, chloramphenicol, fosfomycin, metronidazole, tigecycline, trimethoprim, or a combination or derivative thereof.

In embodiments where the sample can comprise fungi, the anti-infective can comprise an anti-fungal. For example, the anti-fungal can comprise Amphotericin B, Anidulafungin, Caspofungin, Fluconazole, Flucytosine, Itraconazole, Ketoconazole, Micafungin, Posaconazole, Ravuconazole, Voriconazole, or a combination or derivative thereof.

As previously discussed, in some embodiments, the anti-infectives can be pre-loaded or otherwise present within test wells of the well plate 104. In other embodiments, the anti-infectives can be added or otherwise introduced into the test wells of the well plate 104 prior to adding aliquots of the sample to the wells 105 of the well plate.

In some embodiments, the anti-infectives within the test wells can be lyophilized or dried. In other embodiments, the anti-infectives within the test wells can be in aqueous form.

The method can further comprise introducing aliquots of a sample comprising the infectious agent into wells 105 of the well plate 104. As previously discussed, the wells 105 can comprise test wells and control wells (e.g., positive control wells).

In some embodiments, the well plate 104 can comprise a plurality of anti-infectives such that certain wells 105 of the well plate 104 are dedicated to certain anti-infectives. In other embodiments, the well plate 104 can comprise only one type of anti-infective.

The method can further comprise placing the sensor array lid 102 on top of the well plate 104 filled with the aliquots of the sample or covering the well plate 104 with the sensor array lid 102.

As previously discussed, the sensor array lid 102 can comprise a plurality of sensor units 112 extending from an underside of the sensor array lid 102. Each of the sensor units 112 can be configured to extend into a well 105 of the well plate 104 such that the sensor units 112 are at least partially immersed in the aliquots of the sample within the wells 105 when the sensor array lid 102 is placed on top of the well plate 104 or covers the well plate 104.

The method can also comprise inserting the well plate 104 covered by the sensor array lid 102 into the reader 700 or otherwise loading the well plate 104 covered by the sensor array lid 102 into the reader 700. The reader 700 can comprise conductive contacts or connections for electrically contacting the active electrodes 118 and the reference electrodes 120 of the sensor units 112.

In some embodiments, the assembled testing device 100 (the well plate 104 covered by the sensor array lid 102) within the reader 700 can be incubated within the reader 700 at an incubation temperature of between about 30° C. and about 40° C.

The method can further comprise determining the susceptibility of the infectious agent to the anti-infectives based on any changes in a solution characteristic of the aliquots of the sample within the test wells comprising the anti-infectives and any changes in the solution characteristic of the aliquots of the sample within the control wells over a period of time.

In some embodiments, the reader can monitor for microbial growth within the wells 105 by tracking or monitoring a change (or lack thereof) in the solution characteristic of the aliquots of the sample within the test wells and the control wells. The reader can then compare any changes in the solution characteristic of the aliquots of the sample within the test wells with any changes in the solution characteristic of the aliquots of the sample within the control wells to determine the susceptibility of the infectious agent to the anti-infectives.

The reader 700, along with one or more computing devices communicatively coupled to the reader 700, can analyze signals obtained from the plurality of sensor units 112 of the testing device 100 and provide information concerning the susceptibility of the infectious agent to the anti-infectives (e.g., levels of susceptibility), along with information concerning minimum inhibitory concentrations (MIC s).

In some embodiments, the results of the testing procedure (e.g., MICs and level of susceptibility) can be obtained and displayed or otherwise conveyed between four hours and up to 10 hours. In certain embodiments, the results of the testing procedure (e.g., MICs and level of susceptibility) can be obtained and displayed or otherwise conveyed between two hours and four hours.

FIG. 9A is a table illustrating performance results for 293 gram-negative contrived PBCs in the presence of several antibiotics. The antibiotics include amikacin (AMK), ceftriaxone (CRO), aztreonam (ATM), cefazolin (CFZ), imipenem (IPM), piperacillin tazobactam (TZP), and trimethoprim sulfamethoxazole (SXT).

The contrived PBCs were prepared in standard aerobic bottles using 293 frozen gram-negative isolates obtained from the Center for Disease Control (CDC) and various hospitals. The 293 contrived PBCs were processed within five hours of flag time and tested in singlet.

The gram-negative isolates included *E. coli, Klebsiella* spp., *Enterobacter* spp., *P. aeruginosa, A. Baumannii, S. marcesans, Proteus* spp., and *Citrobacter* spp.

All contrived PBCs were diluted using Mueller Hinton broth (MHB) and aliquots of the diluted samples were transferred to wells 105 of several well plates 104 (e.g., 96-well well plates 104). Testing wells contained the seven clinically-significant antibiotics mentioned above in lyophilized form.

A sensor array lid 102 was placed on top of the well plate 104 comprising the diluted PBCs. The entire testing device 100 was then loaded into the reader 700 for antimicrobial susceptibility testing. Results for certain antibiotics were obtained in as little as four hours (see FIG. 9C).

Clinical and Laboratory Standards Institute (CLSI) Interpretations (see CLSI. *Performance Standards for Antimicrobial Susceptibility Testing*. 30th ed. CLSI supplement M100) were applied and all MIC results were compared to MICs determined using a standard broth microdilution. The broth microdilutions were prepared using 0.5 McFarland standard samples diluted according to manufacturer recommended guidelines. The results of the broth microdilutions were manually read following 21 hours of incubation time.

As shown in FIG. 9A, essential agreement (EA), categorical agreement (CA), minor discrepancy (mD), major discrepancy (MD), and very major discrepancy (VMD) rates were calculated according to FDA guidelines. The tests yielded an overall EA of 98.1% and a CA of 95.2% with an mD rate of 4.0%, a MD rate of 1.1%, and a VMD rate of 0.4%. These results easily meet the FDA proposed criteria of >90% EA and CA, with <3% MD, and <3% VMD. This demonstrates that the system, devices, and methods disclosed herein can produce accurate AST results compared to methods currently considered the gold-standard in the field.

FIG. 9B is a table illustrating performance results for 34 prospective gram-negative PBCs in the presence of several antibiotics. The antibiotics include AMK, CRO, ATM, CFZ, IPM, TZP, and SXT.

The prospective PBCs were obtained from a local hospital. The 34 prospective PBCs were processed within 12 hours of flag time and tested in triplet.

The identified bacteria included *E. coli, Klebsiella* spp., *Enterobacter* spp., *P. aeruginosa, S. marcesans,* and *Proteus* spp.

All prospective PBCs were diluted using Mueller Hinton broth (MHB) and aliquots of the diluted samples were transferred to wells 105 of several well plates 104 (e.g., 96-well well plates 104). Testing wells contained the seven clinically-significant antibiotics mentioned above in lyophilized form.

A sensor array lid 102 was placed on top of the well plate 104 comprising the diluted PBCs. The entire testing device 100 was then loaded into the reader 700 for antimicrobial susceptibility testing. Results for certain antibiotics were obtained in as little as four hours.

Clinical and Laboratory Standards Institute (CLSI) Interpretations (see CLSI. *Performance Standards for Antimicrobial Susceptibility Testing.* 30th ed. CLSI supplement M100) were applied and all MIC results were compared to MICs determined using a standard broth microdilution. The broth microdilutions were prepared using 0.5 McFarland standard samples diluted according to manufacturer recommended guidelines. The results of the broth microdilutions were manually read following 21 hours of incubation time.

As shown in FIG. 9B, the tests yielded an overall EA of 96.5% and a CA of 95.0% with an mD rate of 3.0%, a MD rate of 2.5%, and a VMD rate of 0.0%. These results easily meet the FDA proposed criteria of >90% EA and CA, with <3% MD, and <3% VMD. This demonstrates that the system, devices, and methods disclosed herein can produce accurate AST results compared to methods currently considered the gold-standard in the field.

Figure 9C:
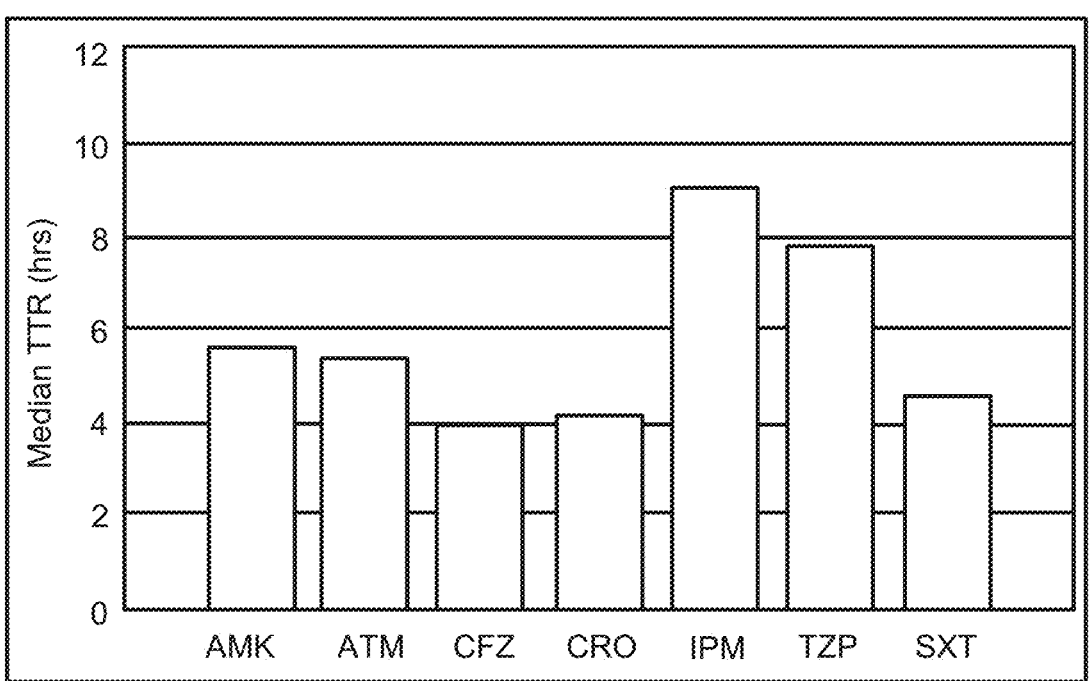
FIG. 9C is a graph showing the times-to-result for the gram-negative contrived PBCs shown in FIG. 9A.

FIG. 9C is a graph showing the times-to-result (TTRs), in hours, for the gram-negative contrived PBCs discussed above in relation to FIG. 9A. As shown in FIG. 9C, the TTRs for gram-negative PBCs in cefazolin (CFZ) and ceftriaxone (CRO) were close to 4 hours with the TTRs for other anti-infectives ranging between 5 hours and 9 hours. Since results obtained using standard broth microdilutions require upwards of 21 hours, FIG. 9C demonstrates that the system, devices, and methods disclosed herein can produce accurate AST results in significantly less time than standard methods.

Figure 10A:
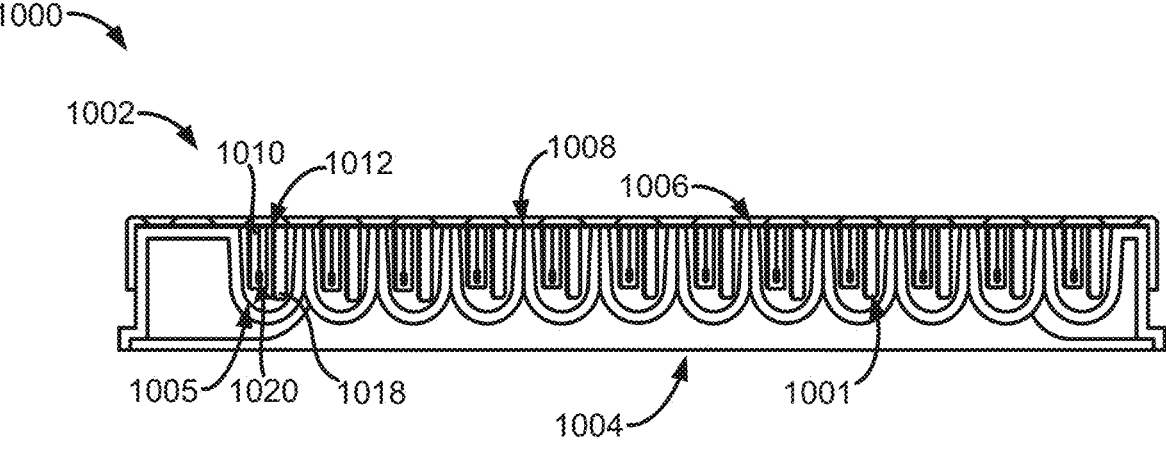
FIG. 10A illustrates a side cross-sectional view of another embodiment of a testing device comprising a sensor array lid comprising sensor units with active electrodes implemented as pins extending into wells of a well plate.

FIG. 10A illustrates a side cross-sectional view of another embodiment of a testing device 1000 comprising a sensor array lid 1002 comprising sensor units 1012 with active electrodes 1018 implemented as pins 1001 extending into wells 1005 of a well plate 1004.

The testing device 1000 shown in FIG. 10A can be similar to the testing device 100 shown in FIGS. 1A-1H except each of the sensor units 1012 comprise an active electrode 1018 made of a pin 1001 coated by a redox-active material. In some embodiments, the redox-active material can be a noble metal. For example the redox-active material can be platinum, gold, or a combination or alloy thereof. As a more specific example, the active electrode 1018 can be implemented as a platinum coated pin 1001.

The testing device 1000 can also be used as part of a system to determine the susceptibility of an infectious agent to an anti-infective. For example, the entire testing device 1000 (including the well plate 1004 covered by the sensor array lid 1002) can be inserted or otherwise introduced into a receiving slot 702 of a reader 700 (see FIGS. 7A and 7B). The system can assay the samples within the wells 1005 for microbial growth or lack thereof as part of an antibiotic susceptibility testing (AST) procedure.

As shown in FIG. 10A, the sensor array lid 1002 can be configured to cover or cap the well plate 1004 when placed on top of the well plate 1004. The well plate 1004 can comprise a plurality of wells 1005 or microwells. For example, the well plate 1004 can comprise between 12 wells and 192 wells. As a more specific example, the well plate 1004 can comprise between 64 wells and 96 wells.

Each of the wells 1005 can be designed to receive a sample comprising an infectious agent. The sample can be diluted prior to introducing aliquots of the sample to the wells 1005. In certain embodiments, the well plate 104 can be a commercially-available or off-the-shelf well plate such or microtiter plate.

The sensor array lid 1002 can comprise a lid top 1006 and a flexible substrate 1008 coupled to the underside of the lid top 1006.

In the embodiment of the testing device 1000 shown in FIG. 10A, the flexible substrate 1008 can comprise a plurality of substrate strips 1010 or substrate segments partially cut out or otherwise separated from a remainder of the flexible substrate 1008 (i.e., the parts of the flexible substrate 1008 coupled to the underside of the sensor array lid 1002). The substrate strips 1010 can be curled or bent vertically downward relative to a surrounding portion of the flexible substrate 1008. The substrate strips 1010 can maintain its curled or bent configuration even when the sensor array lid 1002 covers or caps the well plate 1004. In this embodiment, the substrate strips 1010 can comprise a reference electrode 1020 disposed on the substrate strip 1010. For example, the reference electrode 1020 can be screen-printed, sputter deposited, or electroplated onto the substrate strips 1010.

The reference electrode 1020 can comprise a reference electrode material. In some embodiments, the reference electrode material can comprise at least one of silver/silver chloride (Ag/AgCl) and carbon. For example, when the reference electrode material is Ag/AgCl or carbon, the reference electrode material can be screen-printed onto the substrate strip 1010.

The reference electrode 1020 can be considered a pseudo reference electrode since the reference electrode 1020 operates without a reference buffer.

The reference electrode material can be coated by an ion exchange membrane or an ionomer coating. In some embodiments, the ion exchange membrane can be a sulfonated tetrafluoroethylene based fluoropolymer-copolymer or a polyaromatic polymer anion exchange membrane. The ion exchange membrane can be screen printed onto the reference electrode material and part of the substrate strip 1010.

The sensor array lid 1002 can also comprise a plurality of active electrodes 1018 implemented as pins 1001 extending from an underside of the sensor array lid 1002. The pins 1001 can be coated with a redox-active material (e.g., platinum) to allow the pins 1001 to serve as the active electrodes 1018.

In some embodiments, the pins 1001 can be coupled in part to the flexible substrate 1008. The pins 1001 can also be coupled to the lid top 1006 of the sensor array lid 1002.

The active electrodes 1018 (the coated pins 1001) and the reference electrodes 1020 can be connected to an electrical contact pad on the sensor array lid 1002 by one or more conductive traces. The electrical contact pad can be mounted, connected, or electrically coupled to the flexible substrate 1008.

The contact pad of the sensor array lid 1002 can be electronically connected or coupled to the active electrodes 1018 (e.g., the coated pins 1001) and the reference electrodes 1020 by a plurality of conductive traces. In some embodiments, the conductive traces can be routed along a surface or side of the flexible substrate 1008 (e.g., the side or surface adhered or coupled to the underside of the lid top 1006). The contact pad can be configured to contact or otherwise engage with conductive connections within the reader 700 when the entire testing device 1000 (in the assembled configuration) is inserted or introduced into a receiving slot 702 of the reader 700 to allow the reader 700 to obtain signals from the active electrodes 1018 and the reference electrodes 1020.

In some embodiments, the flexible substrate 1008 can be made, at least in part, of a flexible polymeric material. For example, the flexible substrate 1008 can be made in part of a flexible sheet of polyethylene terephthalate (PET).

The flexible substrate 108 can also be made in part of a flexible printed circuit board (PCB) material. For example, the flexible substrate 1008 can be made in part of polyimide or polyamide.

In alternative embodiments, the flexible substrate 1008 can be made in part of a conductive metal substrate. For example, in these embodiments, the flexible substrate 108 can be made in part of a sheet of stainless steel foil.

In some embodiments, the flexible substrate 1008 can be coupled to the underside of the lid top 1006 by a biocompatible adhesive (e.g., a biocompatible polymeric adhesive, a cyanoacrylate adhesive, etc.) and a fastener (e.g., screws, clips, clasps, etc.).

The sensor array lid 1002 can completely cover or fit over a top of the well plate 1004 when the testing device 1000 is in the assembled configuration. The sensor array lid 1002, including the lid top 1006, can protect the samples within the wells 1005 from contamination and prevent the samples from spilling or inadvertently leaking out.

For purposes of this disclosure, a sensor unit 1012 can refer to a substrate strip 1010 comprising a reference electrode 1020 and an active electrode 1018 implemented as a coated pin 1001 positioned in the same well 1005 as the substrate strip 1010.

In other embodiments, both the active electrode 1018 and the reference electrode 1020 can be implemented as coated pins. In these embodiments, the active electrode 1018 can be pins coated by a redox-active material (e.g., platinum or gold) and the reference electrodes 1020 can be pins coated by a reference electrode material or pins made of a reference electrode material. The pins serving as the reference electrodes can be further coated by an ion exchange membrane or ion exchange coating or ionomer coating).

Each of the sensor units 1012 (for example, implemented as curled or bent substrate strips 110) can extend into a well 1005 of the well plate 1004 when the sensor array lid 1002 covers or caps the well plate 1004. When the wells 1005 of the well plate 1004 are filled with an inoculum/aliquot of the sample, at least part of the sensor unit 1012 can be immersed in the inoculum/aliquot of the sample.

The sensor units 1012 can be aligned to match the alignment or arrangement of the wells 1005. For example, when the well plate 1004 comprises 96 wells arranged as an 8×12 array of wells 1005, the sensor array lid 1002 can comprise 96 sensor units 1012 arranged as an 8×12 array of sensor units 1012.

Figure 10B:
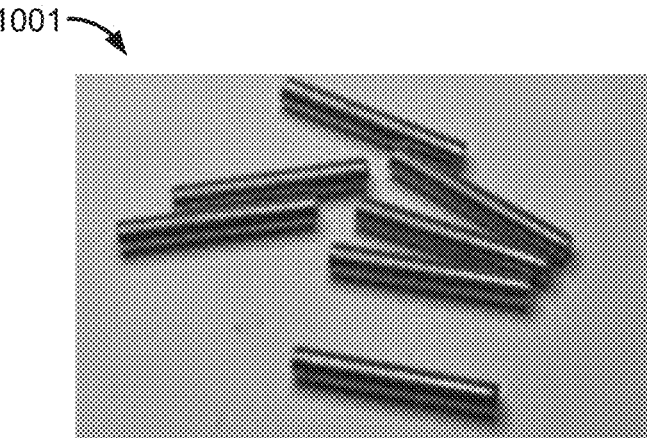
FIG. 10B is a black-and-white image illustrating platinum coated pins serving as active electrodes.

FIG. 10B is a black-and-white image illustrating platinum coated pins 1001 serving as active electrodes 1018 of the sensor array lid 1002. As shown in FIG. 10B, the pins 1001 can be shaped as miniature cylindrical rods.

In some embodiments, the platinum coated pins 1001 can be coupled to the flexible substrate 1008 via a biocompatible adhesive. In other embodiments, the platinum coated pins 1001 can be coupled to the flexible substrate 1008 via a mechanical fastening or fixation mechanism (e.g., threaded connections, interference fit, etc.).

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A sensor array lid, comprising:
a lid top;
a flexible substrate coupled to an underside of the lid top, wherein the flexible substrate comprises a plurality of substrate strips or segments partially cut out from a remainder of the flexible substrate, wherein at least one substrate strip or segment of the flexible substrate curls or bends vertically downward relative to a surrounding portion of the flexible substrate;
an active electrode disposed on each of the substrate strips or segments curling or bending vertically downward; and
a reference electrode disposed on each of the substrate strips or segments curling or bending vertically downward.

2. The sensor array lid of claim 1, wherein the active electrode comprises a redox-active material.

3. The sensor array lid of claim 2, wherein the redox-active material is a noble metal.

4. The sensor array lid of claim 2, wherein the redox-active material is a metal oxide.

5. The sensor array lid of claim 1, wherein the reference electrode comprises a reference electrode material.

6. The sensor array lid of claim 5, wherein the reference electrode material comprises at least one of silver/silver chloride (Ag/AgCl) and carbon.

7. The sensor array lid of claim 6, wherein the reference electrode material is coated or covered by an ion exchange membrane.

8. The sensor array lid of claim 7, wherein the ion exchange membrane is a sulfonated tetrafluoroethylene-based fluoropolymer-copolymer or a polyaromatic polymer anion exchange membrane.

9. The sensor array lid of claim 1, wherein the lid top comprises posts extending from the underside of the lid top, wherein the posts are configured to push or press against the substrate strips or segments such that the substrate strips or segments maintain their curled or bent configuration.

10. The sensor array lid of claim 9 wherein at least one of the substrate strips or segments is pushed or pressed by at least one of the posts such that a portion of the substrate strip or segment is substantially perpendicular to portions of the flexible substrate that are coupled to the lid top.

11. The sensor array lid of claim 9, wherein the posts extend downward from the underside of the lid top, and wherein the posts are angled to allow the posts to push or press against the substrate strips.

12. The sensor array lid of claim 11, wherein the posts are positioned at an oblique angle with respect to the underside of the lid top.

13. The sensor array lid of claim 1, wherein the flexible substrate is made in part of a flexible polymeric material.

14. The sensor array lid of claim 13, wherein the flexible polymeric material is made in part of at least one of a polyethylene terephthalate (PET) and a flexible printed circuit board (PCB) material.

15. The sensor array lid of claim 1, wherein the flexible substrate is made in part of a conductive metal substrate.

16. The sensor array lid of claim 1, wherein at least one of the active electrode and the reference electrode is a screen printed electrode (SPE) such that at least one of a redox-active material of the active electrode and a reference electrode material of the reference electrode is screen printed onto the flexible substrate.

17. The sensor array lid of claim 1, wherein at least one of the active electrode and the reference electrode is an electroplated electrode such that at least one of a redox-active material of the active electrode and a reference electrode material of the reference electrode is electroplated onto the flexible substrate.

18. The sensor array lid of claim 1, wherein at least one of the active electrode and the reference electrode is a sputter deposited electrode such that at least one of a redox-active material of the active electrode and a reference electrode material of the reference electrode is sputter deposited onto the flexible substrate.

19. The sensor array lid of claim 1, wherein the flexible substrate comprises an electrical contact pad disposed on the flexible substrate, and wherein the electrical contact pad is left exposed by the lid top, wherein the active electrode is electrically connected to the electrical contact pad via conductive traces, and wherein the reference electrode is electrically connected to the electrical contact pad via additional conductive traces.

20. The sensor array lid of claim 1, wherein the reference electrode is a pseudo reference electrode.

* * * * *